United States Patent [19]

Takase et al.

[11] Patent Number: 4,800,201
[45] Date of Patent: * Jan. 24, 1989

[54] 1,4-THIAZINE DERIVATIVE, AND CARDIOTONIC AGENT COMPRISING IT AS EFFECTIVE COMPONENT

[75] Inventors: Muneaki Takase; Kimitomo Yoshioka, both of Tokyo; Hiroaki Yamazaki, Ibaragi, all of Japan

[73] Assignee: Zenyaku Kogyo Kabushiki Kaisha, Tokyo, Japan

[*] Notice: The portion of the term of this patent subsequent to Jan. 21, 2003 has been disclaimed.

[21] Appl. No.: 876,860

[22] PCT Filed: Oct. 3, 1985

[86] PCT No.: PCT/JP85/00548

§ 371 Date: Jun. 3, 1986

§ 102(e) Date: Jun. 3, 1986

[87] PCT Pub. No.: WO86/02074

PCT Pub. Date: Apr. 10, 1986

[30] Foreign Application Priority Data

Oct. 4, 1984 [JP] Japan ............... 59-208781
Mar. 28, 1985 [JP] Japan ............... 60-64679

[51] Int. Cl.⁴ .................. A61K 31/54; C07D 279/12
[52] U.S. Cl. ......................... 514/230.8; 544/58.2
[58] Field of Search .............. 544/58.2; 514/222

[56] References Cited

U.S. PATENT DOCUMENTS 3,378,555 4/1968 Takamizawa et al. ......... 544/58.2
4,483,983 11/1984 Lang et al. ................... 544/58.2
4,565,813 1/1986 Takase et al. ................. 514/222

FOREIGN PATENT DOCUMENTS 138058 4/1985 European Pat. Off. .
48-31115 9/1973 Japan ........................ 544/58.2
58-131981 8/1983 Japan .
59-16889 1/1984 Japan .
769261 3/1957 United Kingdom ............ 544/58.2
2118553 11/1983 United Kingdom ............ 544/58.2

Primary Examiner—John M. Ford
Attorney, Agent, or Firm—Scrivener and Clarke

[57] ABSTRACT

A novel 1,4-thiazine derivative represented by the formula I, a pharmaceutically acceptable acid addition salt thereof, a process for preparation thereof and a cardiotonic agent comprising it as an effective component;

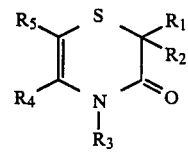

wherein $R_1$ and $R_2$ represent respectively hydrogen atom, lower alkyl group, lower alkoxy group, amino group, lower alkyl-amino group, aryl-amino group, hydroxy group, aryl group or 5- or 6-membered heterocyclic residue;

$R_3$ and $R_4$ represent hydrogen atom or lower alkyl group; and $R_5$ represents N-containing heterocyclic residue and is not pyridinyl group when $R_1$ and $R_2$ represent hydrogen atom and $R_3$ and $R_4$ represent hydrogen atom or lower alkyl group.

33 Claims, No Drawings

1,4-THIAZINE DERIVATIVE, AND CARDIOTONIC AGENT COMPRISING IT AS EFFECTIVE COMPONENT

TECHNICAL FIELD

The present invention relates to a novel 1,4-thiazine derivative represented by the formula I, a pharmaceutically acceptable acid addition salt thereof, a process for preparation thereof and a cardiotonic agent comprising it as an effective component;

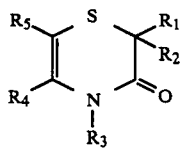

wherein $R_1$ and $R_2$ represent respectively hydrogen atom, lower alkyl group, lower alkoxy group, amino group, lower alkyl-amino group, aryl-amino group, hydroxy group, aryl group or 5- or 6-membered heterocyclic residue;

$R_3$ and $R_4$ represent hydrogen atom or lower alkyl group; and $R_5$ represent N-containing heterocyclic residue and is not pyridinyl group when $R_1$ and $R_2$ represent hydrogen atom and $R_3$ and $R_4$ represent hydrogen atom or lower alkyl group.

BACKGROUND ART

Known process for synthesis of 1,4-thiazine derivative are for example a process starting with a thioglycol amide derivative as disclosed in Journal of the American Chemical Society, 70, 3517 (1948), a process starting with a tricyclic compound as disclosed in Japanese Patent Publication No. 16630/1967 and a process starting with a thiazolium compound as disclosed in Japanese Patent Publication No. 29182/1970.

The fact that pyridone derivatives and pyridazinone derivatives possess properties affecting the cardiovascular systems is described in for example Japanese Patent Provisional Publication No. 48675/1977, Journal of Medicinal Chemistry, 17, 273 (1974) and Japanese Patent Provisional Publication No. 109771/1982.

However, 1,4-thiazine derivatives having nitrogen-containing heterocyclic residue at position 6 are novel compounds and no technique is known for synthesis of such compounds. Furthermore, there is no report on cardiotonic activity of such compounds.

DISCLOSURE OF THE INVENTION

We, the inventors succeeded in synthesis of novel 1,4-thiazine derivatives as disclosed in prior Japanese Patent Application No. 170862/1983. As a result of our further intensive researches, we found that novel 1,4-thiazine derivatives having nitrogen-containing heterocyclic residue at position 6 have cardiotonic activity and completed the present invention. The present invention is directed to a novel 1,4-thiazine derivative having a nitrogen-containing heterocyclic residue at position 6, a pharmaceutically acceptable acid addition salt thereof, a process for preparation thereof and a cardiotonic agent comprising it as an effective component.

Terms used for definition of letters in the above formula I by which the compound of the present invention is represented are defined and exemplified in the following.

The term "lower" refers to group having 1 to 6 carbon atoms unless otherwise indicated.

The "lower alkyl group" may be alkyl group which are arranged as straight or branched chains and may be methyl, ethyl, n-propyl, iso-propyl, n-butyl, iso-butyl, tert-butyl, n-pentyl, n-hexyl or the like.

The "lower alkoxy group" may be methoxy, ethoxy, n-propoxy, iso-propoxy, n-butoxy, iso-butoxy, tert-butoxy, n-pentyloxy, n-hexyloxy or the like.

The "aryl group" may be phenyl, tolyl, xylyl, mesityl, cumenyl, biphenyl or the like which may unsubstituted or may be substituted with lower alkyl group, lower alkoxy group, halogen atom, aldehyde group, acyl group, cyano group, nitro group, hydroxy group or the like.

The term "lower alkyl-amino group" means amino groups substituted with above-mentioned lower alkyl groups. The "lower alkyl-amino group" may be methylamino, dimethylamino, ethylamino, diethylamino, n-hexylamino or the like.

The term "arylamino group" means amino groups substituted with above-mentioned aryl group. The "arylamino" group may be anilino, toluidino, xylidino or the like.

The term "5- or 6-membered heterocyclic residue" means oxygen-, sulfur-, or nitrogen-containing 5- or 6-membered heterocyclic residue. The "5- or 6-membered heterocyclic residue" may be furyl, thienyl, pyrrolyl, pyrano, pyridinyl, pyridazino, pyrimidino, piperidino, piperazino or morpholino or the like.

The term "N-containing heterocyclic residue" means nitrogen-containing 5- or 6-membered mono or condensed heterocyclic residue which may be unsubstituted or may be substituted by lower alkyl group, lower alkoxy group, halogen atom, cyano group, nitro group, aldehyde group, acyl group, hydroxy group, lower alkoxycarbonyl group or the like. The "N-containing heterocyclic residue" may be pyridinyl, pyridazinyl, pyrimidinyl, pyrazinyl, quinolinyl, iso-quinolinyl, cinnolinyl, quinazolinyl, quinoxalinyl, phthalazinyl, acridinyl, methylpyridinyl, methoxypyridinyl, chloropyridinyl, formylpyridinyl, cyanopyridinyl, nitropyridinyl, acetylpyridinyl, hydroxypyridinyl, methoxyquinolinyl, methylpyridazinyl, methoxycarbonylpyridinyl, thiazolyl, piperidinyl, piperadinyl, morpholinyl or the like.

It is to be noted that some of the compounds according to the present invention may be alternatively represented by its tautomers. For example, a compound of the formula I having hydroxy group adjacent to nitrogen atom of pyridine ring may exist in the following two forms.

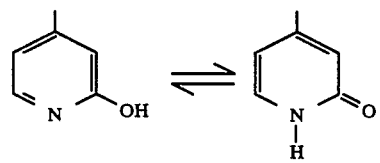

Accordingly all of such isomers are included within the category of the compound of the formula I.

The compounds according to the present invention are for example as follows:

5-methyl-6-(4-quinolinyl)-2H-1,4-thiazin-3(4H)-one;

5-methyl-6-(4-pyridazinyl)-2H-1,4-thiazin-3(4H)-one;
5-methyl-6-(3-chloro-4-pyridinyl)-2H-1,4-thiazin-3(4H)-one;
5-methyl-6-(3-formyl-4-pyridinyl)-2H-1,4-thiazin-3(4H)-one;
5-methyl-6-(3-cyano-4-pyridinyl)-2H-1,4-thiazin-3(4H)-one;
5-methyl-6-(3-methoxycarbonyl-4-pyridinyl)-2H-1,4-thiazin-3(4H)-one;
5-methyl-6-(3-acetyl-4-pyridinyl)-2H-1,4-thiazin-3(4H)-one;
5-methyl-6-(6-methoxy-4-quinolinyl)-2H-1,4-thiazin-3(4H)-one;
5-methyl-6-(3-methyl-4-pyridazinyl)-2H-1,4-thiazin-3(4H)-one;
5-methyl-6-(3-methyl-4-pyridinyl)-2H-1,4-thiazin-3(4H)-one;
5-methyl-6-(2-thiazolyl)-2H-1,4-thiazin-3(4H)-one;
2,5-dimethyl-6-(4-pyridinyl)-2H-1,4-thiazin-3(4H)-one;
2-ethyl-5-methyl-6-(4-pyridinyl)-2H-1,4-thiazin-3(4H)-one;
2-methoxy-5-methyl-6-(4-pyridinyl)-2H-1,4-thiazin-3(4H)-one;
2,2-dimethoxy-5-methyl-6-(4-pyridinyl)-2H-1,4-thiazin-3(4H)-one;
2-amino-5-methyl-6-(4-pyridinyl)-2H-1,4-thiazin-3(4H)-one;
2-diethylamino-5-methyl-6-(4-pyridinyl)-2H-1,4-thiazin-3(4H)-one;
2-hydroxy-5-methyl-6-(4-pyridinyl)-2H-1,4-thiazin-3(4H)-one;
2-(4-hydroxyphenyl)-5-methyl-6-(4-pyridinyl)-2H-1,4-thiazin-3(4H)-one;
5-methyl-2-phenylamino-6-(4-pyridinyl)-2H-1,4-thiazin-3(4H)-one;
2-(2-furyl)-5-methyl-6-(4-pyridinyl)-2H-1,4-thiazin-3(4H)-one;
5-methyl-2-(2-thienyl)-6-(4-pyridinyl)-2H-1,4-thiazin-3(4H)-one;
5-methyl-2-(2-pyrrolyl)-6-(4-pyridinyl)-2H-1,4-thiazin-3(4H)-one;
2,5-dimethyl-6-(4-pyridazinyl)-2H-1,4-thiazin-3(4H)-one;
2,5-dimethyl-6-(4-quinolinyl)-2H-1,4-thiazin-3(4H)-one;
2,5-dimethyl-6-(3-methoxy-4-pyridinyl)-2H-1,4-thiazin-3(4H)-one;
2,5-dimethyl-6-(6-methoxy-4-quinolinyl)-2H-1,4-thiazin-3(4H)-one;
2,5-dimethyl-6-(3-acetyl-4-pyridazinyl)-2H-1,4-thiazin-3(4H)-one;
5-methyl-2-piperidino-6-(4-pyridinyl)-2H-1,4-thiazin-3(4H)-one;
5-methyl-2-morpholino-6-(4-pyridinyl)-2H-1,4-thiazin-3(4H)-one;
or the like.

The compound of the formula I according to the present invention is prepared for example according to the following alternative methods.

First method:
When a 1,4-thiazine derivative of the formula III (in which $R_1$, $R_2$, $R_3$, and $R_4$ are as defined above) is reacted with a known compound of the formula A—X' (in which A represents a residue

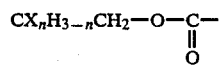

in which X represents a halogen atom and n is an integer of 1 to 3 and X' represents a halogen atom which may be the same as or different from X) and a known compound of the formula $R_5$—H (in which $R_5$ is as defined above), a novel 1,4-thiazine derivative of the formula II is obtained.

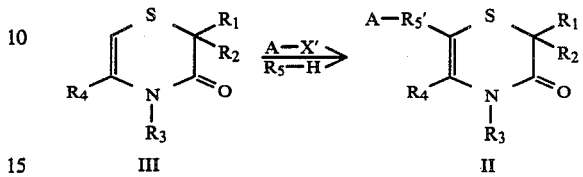

wherein $R_1$, $R_2$, $R_3$, $R_4$ and A are as defined above and $R_5'$ represents dihydro form residue of N-containing heterocyclic group.

This reaction is completed by merely mixing equal mole concentration of the compound of the formula III and the compound of the formula A—X' and more than equal mole concentration of the compound of the formula $R_5$—H under atmospheric pressure at ambient temperature, and stirring the mixture in the presence of a solvent for more than 30 minutes preferably from 1 to 7 hours.

The solvent used in this reaction may be nitrile such as acetonitrile, ether such as tetrahydrofran, halogenated hydrocarbon such as dichloromethan or the like. Alternatively, the compound having N-containing heterocyclic residue itself may also be used as the solvent.

The compound having N-containing heterocyclic residue may be pyridine, pyridazine, pyrimidine, pyrazine, quinoline, isoquinoline, cinnoline, quinazoline, quinoxaline, phthalazine, acridine, phenazine, thiazole, piperidine, piperazine, morpholine or the like, or derivative thereof having substituent such as lower alkyl group, lower alkoxy group, halogen atom, cyano group, nitro group, aldehyde group, acyl group, hydroxy group or the like. Such derivative may be 3-methoxypyridine, 3-chloropyridine, pyridine-3-aldehyde, 3-methylpyridine, nicotinonitrile, 3-acetylpyridine, methyl nicotinate, 3-nitropyridine, 3-hydroxypyridine, 6-methoxyquinoline, 3-methylpyridazine or the like.

Then, the residue A of the above-mentioned compound of the formula A—X' connected to position 6 of the compound of the formula II, that is halogenated ethoxycarbonyl group is removed to thereby obtain a compound of the formula I.

This may be effected in various ways; a typical way is as follows.

The compound of the formula II is reacted with sulfur at elevated temperature to remove the residue. More specifically, the compound of the formula II is stirred with 5 fold amount of finely ground sulfur and the mixture is heated under atmospheric pressure at 120° to 200° C. for 0.5 to 8 hours, preferably at 140° C. to 180° C. for 1 to 5 hours to obtain a compound of the formula I. Generally, no solvent is needed in this reaction; however, N,N-dimethylformamide, dimethyl sulfoxide, etc. may be employed. In the case of using such solvent, the amount of sulfur may be substantially half as much as that of the compound of the formula II.

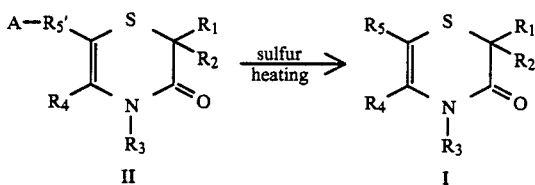

wherein $R_1$, $R_2$, $R_3$, $R_4$, $R_5$, A and $R_5'$ are as defined above.

Alternatively, the compound of the formula II may be reacted with zinc at elevated temperature for such removal. In this case, the substituent at position 6 is still a dihydro residue so that oxidation is needed for obtaining an intended compound of the formula I. More specifically, the compound of the formula II is reacted with excessive amount of zinc under atmospheric pressure at 30° to 80° C. for 1 to 4 hours, preferably 50° to 60° C. for 2 to 3 hours in the presence of a solvent. Then, an oxidizing agent such as 2,3-dichloro-5,6-dicyano-p-benzoquinone (DDQ) is added thereto and the mixture is stirred at 30° to 80° C. for 1 to 4 hours, preferably 50° to 60° C. for 2 to 3 hours to obtain a compound of the formula I. A solvent used in this reaction may be nitrile such as acetonitrile, ether such as tetrahydrofuran, sulfoxide such as dimethylsulfoxide, amide such as dimethylformamide or the like.

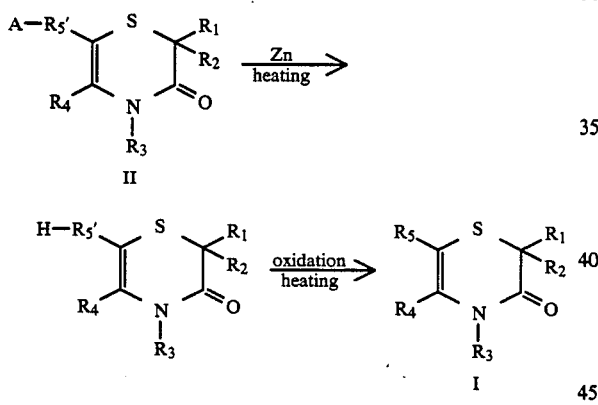

wherein $R_1$, $R_2$, $R_3$, $R_4$, $R_5$, A and $R_5'$ are as defined above.

Purification of the compounds of the formula I and II may be accomplished by recrystallization from lower alcohol such as methanol, ethanol or isopropanol, ketone such as acetone, halogenated hydrocarbon such as chlorofrom, carboxylic acid ester such as ethyl acetate, aromatic hydrocarbon such as benzene, ether such as diethylether or nitrile such as acetonitrile or the like.

Alternatively, such purification may also be accomplished by column chromatography, flash column chromatography or thin layer chromatography using silica gel. Preferably used in column chromatography is silica gel having particle size of 100–200 mesh such as Wakogel C-200 (manufactured by Wako Pure Chemical Industries, Ltd., in Japan); in the case of flash column chromatography, silica gel having particle's porous diameter of 40–63μ such as silica gel 60 (Art 9385) (manufactured by Merck & Co. Inc. in USA); and in the case of thin layer chromatography, silica gel having particle's average porous diameter of 6 nm which fluoresces in the region of 254 nm such as Merck TCL plate silica gel 60F$_{254}$ (manufactured by Merck & Co. Inc. in USA).

The compound of the formula II may be directly used in the subsequent step, without purification.

The starting material 1,4-thiazine derivative of the formula III may be prepared in the following ways.

The starting material of the formula III wherein $R_3$ is a hydrogen atom may be prepared according to the ways proposed by H. Sokol et al. in J. Am. Chem. Soc., 70, 3517 (1948), C. R. Johnson et al. in J. Hetero. Chem., 6, 247–249 (1969) and G. V. Rao et al. in Synthesis, 136 (1972).

The starting material of the formula III wherein $R_3$ is lower alkyl group may be prepared according to the ways proposed by G. D. Stevens et al. in J. Am. Chem. Soc. 80, 5198 (1958) and M. Hojo et al. in Synthesis, 272 (1979).

In view of the state of the reaction system (the reactivity and degree of dissociation) and the easy availability, an especially preferred compound of the formula A—X' is one in which X and X' represent chlorine atom and n is 3, i.e. 2,2,2-trichloroethylchloroformate.

Second method:

1,4-Thiazine derivative having substituent at position 2 may be obtained by following steps.

1,4-Thiazine derivative with no substituent at position 2, i.e. the compound of the formula I''', is prepared according to the first method described above.

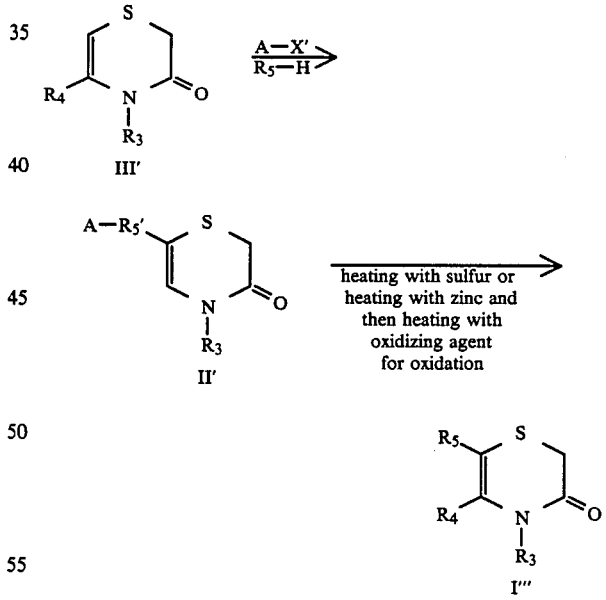

wherein $R_3$, $R_4$, $R_5$, A and $R_5'$ are as defined above.

Then the substituent is introduced to position 2 of the compound of the formula I''' according to the way proposed by M. Hojo et al. in Synthesis, 312, 424 (1982) or the like. More specifically, the compound of the formula I''' is reacted with a peracid of the formula A'—COOOH (in which A' represents lower alkyl group, alicyclic compound residue or aryl group) to obtain a novel, 1,4-thiazine derivative represented by the compound of the formula IV.

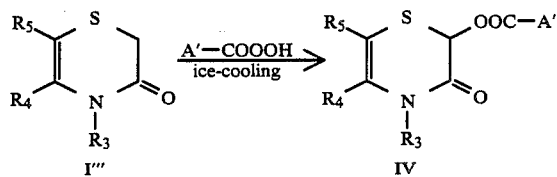

ps wherein $R_3$, $R_4$, $R_5$ and $A'$ are as defined above.

This reaction is completed by merely mixing substantially equal mole concentration of the compound of the formula $I'''$ and the compound of the formula $A'$—COOOH under atmospheric pressure and ice-cooling and stirring the mixture in the presence of solvent for a few minutes.

The solvent, which is used in this reaction, may be halogenated hydrocarbon such as dichloromethane, nitrile such as acetonitrile, ether such as tetrahydrofran, sulfoxide such as dimethylsulfoxide or amide such as dimethylformamide or the like.

As for the peracid, aliphatic peroxycarboxylic acid such as performic acid or peracetic acid, alicyclic peroxycarboxylic acid such as cyclohexaneperoxycarboxylic acid, aromatic peroxycarboxylic acid such as perbenzoic acid or monoperoxyphthalic acid, or derivative thereof may be employed. In view of the state of the reaction system (the reactivity and degree of dissociation) and the easy availability, m-chloroperbenzoic acid is especially preferred.

Then, the compound of the formula IV is reacted with a nucleophilic reagent of the formula $R_1'$—H (in which $R_1'$ is lower alkoxy group, amino group, lower alkyl-amino group, aryl-amino group, hydroxy group, aryl group or 5- or 6-membered heterocyclic residue) to obtain an intended compound of the formula $I''$.

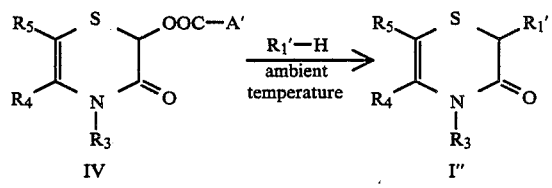

wherein $R_1'$, $R_3$, $R_4$, $R_5$ and $A'$ are as defined above.

This reaction is completed by merely mixing substantially equal mole concentration of the compound of the formula IV and compound of the formula $R_1'$—H under atmospheric pressure at ambient temperature and stirring the mixture in the presence of a solvent.

Alternatively, for accelaration of the reaction the reaction may be carried out at the elevated temperature of 50°–70° C.

In this reaction, amide such as dimethylformamide, nitrile such as acetonitrile, ether such as tetrahydrofran, sulfoxide such as dimethylsulfoxide or halogenated hydrocarbon such as dichloromethane or the like may be used as a solvent. Alternatively, the compound of the formula $R_1'$—H itself may be used as a solvent.

As for the nucleophilic reagent of the formula $R_1'$—H, lower alcohol such as methanol, ethanol or iso-propanol, ammonium salt such as ammonium carbonate, amine such as methylamine or diethylamine, aryl-amine such as aniline, aromatic compound such as phenol, heterocyclic compound such as furan, piperazine, morphorine, thiophene, pyrrole, imidazole or water or the like may be employed.

Introduction of a substituent except for hydrogen atom at position 2 may be similarly carried out such that the compound of the formula $I''$ is reacted with a nucleophilic reagent of the formula $R_2'$—H (in which $R_2'$ represents lower alkoxy group, amino group, lower alkyl-amino group, aryl-amino group, hydroxy group, aryl group or 5- or 6-membered heterocyclic residue).

As for the nucleophilic reagent of the formula $R_2'$—H, lower alcohol such as methanol or ethanol, ammonium salt such as ammonium carbonate, amine such as methylamine or diethylamine, aryl-amine such as aniline, aromatic compound such as phenol, heterocyclic compound such as furan, piperazine, morphorine, thiophene, pyrrole or imidazole, water or the like may be employed.

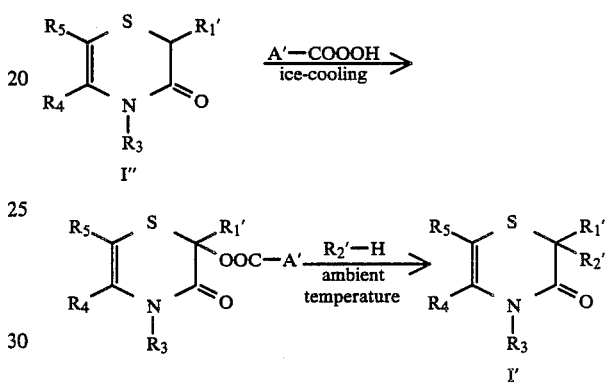

wherein $R_1'$, $R_3$, $R_4$, $R_5$, $A'$ and $R_2'$ are as defined above.

This reaction is completed by mixing the compound of the formula $I''$, with the compound of the formula $A'$—COOOH under atmospheric pressure and ice-cooling and stirring the mixture in the presence of a solvent for reaction, and adding a compound of the formula $R_2'$—H to the reaction mixture under atmospheric pressure at ambient temperature, and stirring the mixture in the presence of a solvent for reaction. For acceleration of the reaction the reaction may be carried out at the elevated temperature of 50°–70° C. The compound of the formula $I'$ in which substituents $R_1'$ and $R_2'$ at position 2 are the same may be obtained by reacting one mole concentration of the compound of the formula $I''$ with more than two mole concentration of the compound of the formula $A'$—COOOH and compound of the formula $R_1'$—H.

The first method is preferable to use when the substituents $R_1$ and $R_2$ at position 2 of the compound of the formula I are hydrogen atom, lower alkyl group or lower alkoxy group, In the other cases, the second method is preferable to use.

The compound of the formula I may be converted into a pharmaceutically acceptable salt by using an appropriate acid.

Such appropriate acid is, for example, inorganic acid such as hydrochloric, hydrobromic, sulfuric, nitric or phosphoric acid, or organic acid such as acetic, propionic, glycolic, lactic, pyruvic, malonic, succinic, maleic, fumaric, malic, tartaric, citric, benzoic, cinnomic, manderic, methanesulfonic, hydroxyethanesulfonic, benzenesulfonic, p-toluenesulfonic, cyclohexanesulfamic, salicyclic, p-aminosalicylic, 2-phenoxybenzoic or 2-acetoxybenzoic acid.

The pharmacological effects of the compound of the formula I will now be described;

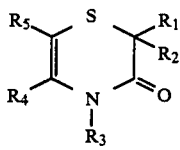

wherein $R_1$, $R_2$, $R_3$, $R_4$ and $R_5$ are as defined above.

Apparatuses used in the following pharmacological tests are

Magnus' bath: supplied by Kabushiki Kaisha Natsume Seisakusho

Pen-writing oscillograph: supplied by Nippon Koden Kabushiki Kaisha

Force displacement pickup: supplied by Nippon Koden Kabushiki Kaisha

Strain pressure amplifier: supplied by Nippon Koden Kabushiki Kaisha

Electrically simulating device: supplied by Nippon Koden Kabushki Kaisha

Pharmacological Test 1

Effect on isolated left atrium of guinea pig was tested according to the method described in Basic Lectures of Medicine Development, Volume V, Pharmacological Test Methods, Part 2, page 534 (1971) published by Chizin Shokan Kabushiki Kaisha in Japan. A 7-weeks-old male Hartley guinea pig (having body weight of about 350 g) was stunned by a blow on the head. The heart was cut out, and the left atrium was taken out in Krebs-Henseleit solution (prepared by adding distilled water for injection to 6.92 g of sodium chloride, 0.35 g of potassium chloride, 0.28 g of calcium chloride, 0.29 g of magnesium sulfate, 0.16 g of mono-basic potassium phosphate, 2.1 g of sodium bicarbonate and 1.8 g of glucose so that the total amount was 1000 ml) which was sufficiently bubbled with oxygen gas. The isolated left atrium was suspended in Magnus' bath at 30° to 32° C. and isometric contraction was recorded by the pen-writing oscillograph through the strain pressure amplifier connected to the force displacement pickup.

The atrium was stimulated electrically at 0.5 cps for 5 msec under a voltage of 20% above threshold. The nutritive liquid was Krebs-Henseleit solution through which 95% oxygen gas and 5% carbon dioxide was blown. Effect of each sample was tested 60 to 90 minutes after stimulation at which the generated tension became stable. The results are shown in Table 1. In this test, corresponding concentration of each sample was $1 \times 10^{-4}$ mole.

TABLE 1

| Effect on Isolated Left Atrium of Guinea Pig | | | | | |
|---|---|---|---|---|---|
| Compound of the formula I of the Invention | | | | | Tension increment |
| $R_1$ | $R_2$ | $R_3$ | $R_4$ | $R_5$ | (mg) |
| —H | —H | —H | —CH$_3$ | quinolinyl-phenyl | 300 ± 125 |
| —H | —H | —H | —CH$_3$ | pyrazinyl-phenyl | 225 ± 123 |
| —H | —H | —H | —CH$_3$ | pyridyl-phenyl (Cl) | 426 ± 56 |
| —H | —H | —H | —CH$_3$ | pyridyl-phenyl (CHO) | 278 ± 56 |
| —H | —H | —H | —CH$_3$ | pyridyl-phenyl (CN) | 214 ± 56 |
| —CH$_3$ | —H | —H | —CH$_3$ | pyridyl-phenyl | 780 ± 93 |

TABLE 1-continued

Effect on Isolated Left Atrium of Guinea Pig

| Compound of the formula I of the Invention | | | | | Tension increment (mg) |
|---|---|---|---|---|---|
| $R_1$ | $R_2$ | $R_3$ | $R_4$ | $R_5$ | |
| —$C_2H_5$ | —H | —H | —$CH_3$ | [N-phenyl ring] | 925 ± 32 |
| [phenyl-OH] | —H | —H | —$CH_3$ | [N-phenyl ring] | 230 ± 92 |
| —$NHCH_3$ | —H | —H | —$CH_3$ | [N-phenyl ring] | 233 ± 46 |
| [morpholino —N(CH₂CH₂)₂O] | —H | —H | —$CH_3$ | [N-phenyl ring] | 207 ± 47 |

It was confirmed that administration of the compound according to the present invention will drastically increase the contractile force of cardiac muscle.

Pharmacological Test 2

Effect on isolated auricule was tested according to the method of L. J. Mcleod described in Pharmacological Experiments on Intact Preparations, pages 112-115 (1970). A 7-weeks-old male Hartley guinea pig (having body weight of about 350 g) was killed by a blow on the head. The heart was cut out, and all the tissues except for the auricule were cut away in Ringer-Locke solution (prepared by adding distilled water for injection to 9.0 g of sodium chloride, 0.25 g of potassium chloride, 0.15 g of calcium chloride and 1.0 g of glucose so that the total amount was 1000 ml). One of cotton threads, which were tied to each tip of the auricule, is attached to Magnus' bath and the other to the force displacement pickup. The Magnus' bath was maintained at 30°±1° C. through which oxygen gas was bubbled. When the rhythmic movement and contraction of cardiac muscle became constant, recording by the pen-writing oscillograph was started. After 1 minute, sample compound was injected and recording was conducted for 5 minutes. After completion of recording, the isolated auricule was washed with Ringer-Locke solution until the rhythmic movement and contraction of cardiac muscle became constant. After 30 minutes, recording by the pen-writing oscillograph was started again. The obtained results are shown in Table 2. In this test, corresponding concentration of each sample was $3 \times 10^{-4}$ mole.

TABLE 2

Effect on Isolated Auricule

| Compound of the formula I of the Invention | | | | | Tension increment (mg) | Increase in heart rate (%) |
|---|---|---|---|---|---|---|
| $R_1$ | $R_2$ | $R_3$ | $R_4$ | $R_5$ | | |
| —H | —H | —H | —$CH_3$ | [N-naphthyl] | 190 | 2.2 |
| —H | —H | —H | —$CH_3$ | [N-phenyl] | 250 | 9.4 |
| —$CH_3$ | —H | —H | —$CH_3$ | [N-phenyl] | 158 | 2.0 |
| —$C_2H_5$ | —H | —H | —$CH_3$ | [N-phenyl] | 226 | 2.4 |

It was confirmed that administration of the compound of the present invention will significantly increase the contractile force of cardiac muscle with little increase of heart rate.

Pharmacological Test 3

The acute toxicity was determined according to the Litchfield-Wilcoxon method, J. Pharm. Exp. Ther., 96, 99 (1947) using 6-weeks-old male ddY mice (having body weight of 19-24 g) while administrating the sample compound in intraperitonial injection. The results are shown in Table 3.

TABLE 3

| Compound of the formula I of the Invention | | | | | LD$_{50}$ (mg/Kg) |
|---|---|---|---|---|---|
| R$_1$ | R$_2$ | R$_3$ | R$_4$ | R$_5$ | |
| —H | —H | —H | —CH$_3$ | 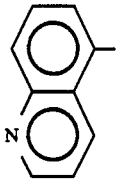 | 270 |
| —H | —H | —H | —CH$_3$ |  | 275 |
| —CH$_3$ | —H | —H | —CH$_3$ |  | 230 |
| —C$_2$H$_5$ | —H | —H | —CH$_3$ |  | 130 |

From the results of the above pharmacological test 1 to 3 the compound of the present invention was found to cause significant increase of contractile force in cardiac muscle with little increase of heart rate and to have low acute toxicity so that the compound of the present invention is effective in curing and preventing heart diseases.

The compound of the present invention may be administrated to human body orally, by injection (intravenously, subcutaneously or intramuscularly) or in any other manner.

When the compound of the present invention is in the form of solid preparations for oral administration, the preparations may be tablets, granules, powders, capsules or the like. The preparations may contain additives, for example, an excipient such as a saccharide or cellulose preparation, a binder such as starch paste or methyl cellulose, a filler, a disintegrator and so on, all being ones usually used in manufacture of medical preparations. In the case where the compound of the present invention is employed as oral liquid preparations, they may be of any form selected from aqueous preparations for internal use, suspensions, emulsions, syrups, etc.; alternatively they may be in the form of dried products which are dissolved prior to the use.

The compound of the present invention may be injected in the form of aqueous solutions, suspensions or oily or aqueous emulsions, but usually the injections are prepared by dissolving or suspending them in aqueous liquid media such as sterile water or physiological saline solutions. If necessary, conventionally used dissolving agents, stabilizers, preservatives, additives for preparing isotonic solutions, etc. may be added to the injections.

BEST MODE FOR CARRING OUT THE INVENTION

The invention will be understood more readily with reference to the following examples; however these examples are intended to illustrate the invention and are not to be constituted to limit the scope of the invention.

In the examples, the mesurements were carried out by using the following apparatuses.

Melting point: Model MP-1 supplied by Yamato Kagaku Kabushiki Kaisha

Mass analysis (MS): Model M-60 supplied by Kabushiki Kaisha Hitachi Seisakusho

Infrared absorption spectrum (IR): Model 260-10 supplied by Kabushiki Kaisha Hitachi Seisakusho Nuclear magnetic resonance (NMR): Model FX-270 supplied by Nippon Denshi Kabushiki Kaisha Elementary analysis: Model MT-2 supplied by Kabushiki Kaisha Yanagimoto Seisakusho

EXAMPLE 1

Preparation of 5-methyl-6-(4-quinolinyl)-2H-1,4-thiazin-3(4H)-one 2,2,2-Trichloroethylchloroformate (4.8 ml) was added dropwise to a suspension of 5-methyl-2H-1,4-thiazin-3(4H)-one (4 g) in dry quinoline (25 ml) under cooling at 0° to 5° C. and the mixture was stirred at ambient temperature for 3 hours. The solvent was removed under reduced pressure and the residue was extracted with chloroform, was washed with 2N hydrochloric acid and successively with water, was dried over magnesium sulfate. The solvent was removed to give dark red oily product (4 g). The oily product (4 g) and sulfur sublimed (20 g) were mixed and stirred at 140°–145° C. for 4 hours and then the mixture was cooled to ambient temperature. The remaining solid was extracted with methanol and the extract was concentrated. The residue was dissolved in 50 ml of 2N hydrochloric acid. The insoluble solid was removed by filtration and the filtrate was adjusted to pH about 7.5 by 2N aqueous sodium hydroxide under cooling and allow to cool overnight. The resulting precipitates were collected by filtration and were chromatographed on silica gel (Wakogel C-200 with 100–200 mesh, manufactured by Wako Pure Chemical Industries, Ltd.) column, using chloroform-methanol (=40:1) as an eluant. The residue was recrystallized from methanol with use of charcoal to give the titled compound (0.66 g, yield 8.4%) as pale orange crystals.

Melting point: 174.5°–175.5° C.

IR spectrum $\nu_{max}^{KBr}$(cm$^{-1}$): 3200, 3100, 1680, 1640

MS spectrum: M+256

NMR spectrum (CDCl$_3$, TMS, δ): 1.77 (3H, s), 3.56 (2H, s), 7.35 (1H, d), 7.60 (1H, t), 7.75 (1H, t), 7.95 (2H, d+s), 8.15 (1H, d) 8.95 (1H, d)

The dark red oily product to be reacted with sulfur sublimed was chromatographed on silica gel (Wakogel C-200) column, using ethyl acetate-n-hexane (=1:1) as an eluant to give 5-methyl-6-[1-(2,2,2-trichloroethoxycarbonyl)-1,4-dihydro-4-quinolinyl]-2H-1,4-thiazin-3(4H)-one as pale yellow crystals.

Melting point: 166°–167° C.

IR spectrum $\nu_{max}^{KBr}$(cm$^{-1}$): 3200, 3060, 1710, 1660, 1630

MS spectrum: M+432

NMR spectrum (CDCl$_3$, TMS, δ): 2.13 (3H, s), 3.12 (2H, ABq), 4.62 (1H, d), 4.93 (2H, s), 5.20 (1H, dd), 7.10–7.30 (4H, m), 7.90 (1H, s), 8.10 (1H, d)

Example 2

(i) Preparation of intermediate:

5-methyl-6-[1-(2,2,2-trichloroethoxycarbonyl)-1,4-dihydro-4-pyridazinyl]-2H-1,4-thiazin-3(4H)-one 2,2,2-Trichloroethylchloroformate (3.44 ml) was added dropwise to a solution of pyridazine (1.44 ml) in dry acetonitrile (40 ml) under ice-cooling, and the mixture was stirred for 10 minutes. 5-Methyl-2H-1,4-thiazin-3(4H)-one (1.29 g) was added to the mixture. The reaction mixture was further stirred at ambient temperature for 1 hour. Then, the solvent was removed under reduced pressure and the residue was extracted with chloroform. The extract was washed with 2N hydrochloric acid and successively with water, was dried over mangnesium sulfate and the solvent was removed. The residue was chromatographed on silica gel (Wakogel C-200) column, using ethyl acetate-n-hexane (=1:1) as an eluant to give the titled compound (2.4 g, yield 63%) as white crystals.

Melting point: 156°-157° C.

IR spectrum $\nu_{max}^{KBr}$(cm$^{-1}$): 3200, 3090, 1740, 1690

MS spectrum: M+383

NMR spectrum (CDCl$_3$, TMS, δ): 2.03 (3H, s), 3.25 (2H, ABq), 4.06 (1H, dd), 4.93 (2H+1H, m), 6.83 (1H, m), 7.22 (1H, d), 8.44 (1H, s)

(ii) Preparation of
5-methyl-6-(4-pyridazinyl)-2H-1,4-thiazin-3(4H)-one 5-methyl-6-[1-(2,2,2-trichloroethoxycarbonyl)-1,4-dihydro-4-pyridazinyl]-2H-1,4-thiazin-3(4H)-one (2.4 g) was well mixed with sulfur sublimed (10.7 g) in a mortar and the mixture was stirred at 140° C. for 1.5 hours and then was cooled to ambient temperature. The obtained solid was ground and was extracted with methanol. Methanol was removed under reduced pressure. The residue was dissolved in 50 ml of 2N hydrochloric acid. The insoluble matter was removed by filtration and the filtrate was adjusted to pH 7.2 by 2N aqueous sodium hydroxide. The resulting precipitates were removed by filtration. The filtrate was extracted with chloroform (20 ml×5 times) and the extract was evaporated to dryness. After combined with the above solid, the residue was recrystallized from methanol to give the titled compound (0.3 g, yield 23%) as pale yellow plates.

Melting point: 231°-233° C.

IR spectrum $\nu_{max}^{KBr}$(cm$^{-1}$): 3200, 3050, 2900, 1670, 1600

MS spectrum: M+207

NMR spectrum (DMSO-d$_6$, TMS, δ): 1.99 (3H, s), 3.46 (2H, s), 7.65 (1H, dd), 9.20 (1H, dd), 9.25 (1H, dd), 10.18 (1H, s)

Example 3

(i) Preparation of intermediate:

5-methyl-6-[1-(2,2,2-trichloroethoxycarbonyl)-3-chloro-1,4-dihydro-4-pyridinyl]-2H-1,4-thiazin-3(4H)-one 3-Chloropyridine (0.88 g), 2,2,2-trichloroethylchloroformate (1.33 ml) and 5-methyl-2H-1,4-thiazin-3(4H)-one (0.5 g) were treated in the same manner as described in Example 2 (i) to give the titled compound (0.75 g, yield 46.3%) as milky white crystals. Chloroform-methanol (=30:1) was used as a developing eluant.

Melting point: 168.5°-171° C.

IR spectrum $\nu_{max}^{KBr}$(cm$^{-1}$): 3190, 3080, 2930, 1720, 1670, 1630

NMR spectrum (CDCl$_3$, TMS, δ): 2.07 (3H, s), 3.28 (2H, s), 4.39 (1H, d), 4.93 (2H+1H, m), 7.10 (1H, d), 7.30 (1H, s), 8.38 (1H, s)

(ii) Preparation of
5-methyl-6-(3-chloro-4-pyridinyl)-2H-1,4-thiazin-3(4H)-one

A mixture of 5-methyl-6-[1-(2,2,2-trichloroethoxycarbonyl)-3-chloro-1,4-dihydro-4-pyridinyl]-2H-1,4-thiazin-3(4H)-one (0.25 g) and sulfur sublimed (0.125 g) in N,N-dimethylformamide (2 ml) was stirred at 160° C. for 5 hours. The solvent was removed under reduced pressure and the residue was extracted with 2N hydrochloric acid. The insoluble matter was removed by filtration and the filtrate was washed with ether and was adjusted to pH about 7.5 by 2N aqueous sodium hydroxide. The resulting precipitates were extracted with chloroform. The extract was dried over magnesium sulfate and was evaporated to dryness. The residue was chromatographed on silica gel (Wakogel C-200) column, using chloroformmethanol (=30:1) as an eluant to give the titled compound (0.083 g, yield 57.8%) as milky white crystals.

Melting point: 169°-171° C.

IR spectrum $\nu_{max}^{KBr}$(cm$-1$): 3200, 3080, 2940, 1630, 1570, 1350

NMR spectrum (CDCl$_3$, TMS, δ): 1.85 (3H, s), 3.49 (2H, s), 7.30 (1H, d), 8.59 (1H, d), 8.76 (1H, s), 9.00 (1H, s)

Example 4

(i) Preparation of intermediate:

5-methyl-6-[1-(2,2,2-trichloroethoxycarbonyl)-3-formyl-1,4-dihydro-4-pyridinyl]-2H-1,4-thiazin-3(4H)-one 2,2,2-Trichloroethylchloroformate (2.13 ml) was added dropwise to a solution of pyridine-3-aldehyde (1.66 g) in dry acetonitrile (50 ml) under ice-cooling, and the mixture was stirred for 0.5 hour. 5-Methyl-2H-1,4-thiazin-3(4H)-one (1.0 g) was added to the mixture. The reaction mixture was further stirred at ambient temperature for 1 hour. The solvent was removed under reduced pressure. The residue was chromatographed on silica gel (Wakogel C-200) column, using ethyl acetate-n-hexane (=1:1) as an eluant. The eluant was recrystallized from ethanol to give the titled compound (1.4 g, yield 44%) as pale yellow crystals.

Melting point: 154°-156° C.

IR spectrum $\nu_{max}^{KBr}$(cm$^{-1}$): 3220, 3050, 2200, 1720, 1660, 1610

NMR spectrum (CDCl$_3$, TMS, δ): 2.17 (3H, s), 3.17 (2H, s), 4.53 (1H, d), 5.13 (2H+1H, s+dd), 7.13 (1H, d), 7.89 (1H, d), 8.23 (1H, s), 9.53 (1H, s)

(ii) Preparation of
5-methyl-6-(3-formyl-4-pyridinyl)-2H-1,4-thiazin-3(4H)-one

A mixture of 5-methyl-6-[1-(2,2,2-trichloroethoxycarbonyl)-3-formyl-1,4-dihydro-4-pyridinyl]-2H-1,4-thiazin-3(4H)-one (0.5 g) and sulfur (2.5 g) was stirred at 160° C. for 3 hours. After cooling, the solid was ground and was extracted with methanol using Soxhlet extractor. Methanol was removed under reduced pressure. The residue was extracted with 40 ml of 2N hydrochloric acid. The insoluble matter was removed by filtration and the filtrate was washed with ether and the water phase was adjusted to pH 7.5 by 2N aqueous sodium hydroxide. The resulting precipitates were extracted with chloroform and were dried. Chloroform was removed under reduced pressure and the residue was purified by the preparative thin layer chromatography [TLC silica gel plate 60F$_{254}$ (supplied by Merck & Co. Inc., U.S.A.), 20×20 cm, thickness 1 mm, chloroform-methanol=40:1] to give the titled compound (0.03 g, yield 10.6%) as pale yellow crystals.

Melting point: 152°–154° C.

IR spectrum $\nu_{max}^{KBr}$(cm$^{-1}$): 3180, 3060, 1660, 1620

NMR spectrum (CDCl$_3$, TMS, δ): 1.85 (3H, s), 3.52 (2H, s), 7.32 (1H, d), 8.45 (1H, s), 8.80 (1H, d), 9.11 (1H, s), 10.23 (1H, s)

Example 5

(i) Preparation of intermediate:

5-methyl-6-[1-(2,2,2-trichloroethoxy-carbonyl)-3-cyano-1,4-dihydro-4-pyridinyl]-2H-1,4-thiazin-3(4H)-one A mixture of nicotinonitrile (1.62 g), 2,2,2-trichloroethylchloroformate (2.13 ml) and 5-methyl-2H-1,4-thiazin-3(4H)-one (1.0 g) was treated in the same manner as described in Example 4 (i) to give the titled compound (0.8 g, yield 25%) as pale yellow crystals. Chloroform-methanol (=20:1) was used as a developing eluant.

Melting point: 189°–191° C. (decomposition)

IR spectrum $\nu_{max}^{KBr}$(cm$^{-1}$): 3200, 3050, 1720, 1660, 1610

NMR spectrum (CDCl$_3$, TMS, δ): 2.08 (3H, s), 3.30 (2H, ABq), 4.36 (1H, d), 4.95 (2H+1H, m), 7.00 (1H, d), 7.62 (1H, s), 7.84 (1H, s)

(ii) Preparation of 5-methyl-6-(3-cyano-4-pyridinyl)-2H-1,4-thiazin-3(4H)-one

A mixture of 5-methyl-6-[1-(2,2,2-trichloroethoxycarbonyl)-3-cyano-1,4-dihydro-4-pyridinyl]-2H-1,4-thiazin-3(4H)-one (0.5 g) and sulfur sublimed (2.5 g) was treated in the same manner as described in Example 4 (ii) to give the titled compound (0.03 g, yield 10.6%) as pale orange powder. Chloroform-methanol (=20:1) was used as a developing eluant.

Melting point: 140°–142° C.

IR spectrum $\nu_{max}^{KBr}$(cm$^{-1}$): 3170, 3050, 2230, 1680 1600

NMR spectrum (CDCl$_3$, TMS, δ): 1.95 (3H, s), 3.50 (2H, s), 7.38 (1H, d), 8.65 (1H, s), 8.90 (1H, d), 8.93 (1H, s)

Example 6

(i) Preparation of intermediate:
5-methyl-6-[1-(2,2,2-trichloroethoxycarbonyl)-3-methoxycarbonyl-1,4-dihydro-4-pyridinyl]-2H-1,4-thiazin-3(4H)-one A mixture of methylnicotinate (2.74 g), 2,2,2-trichloroethylchloroformate (3.44 ml) and 5-methyl-2H-1,4-thiazin-3(4H)-one (1.29 g) was treated in the same manner as described in Example 2 (i) to give the titled compound (2.1 g, yield 48%) as pale yellow crystals. Ethyl acetate-n-hexane (=1:1) was used as a developing eluant.

Melting point: 171°–172° C.

IR spectrum $\nu_{max}^{KBr}$(cm$^{-1}$): 3300, 1730, 1670, 1610

MS spectrum: M$^+$440

NMR spectrum (CDCl$_3$, TMS, δ): 2.10 (3H, s), 3.16 (2H, s), 3.76 (3H, s), 4.47 (1H, d), 4.90 (2H+1H, m), 7.00 (1H, d), 7.82 (1H, s), 8.09 (1H, s)

(ii) Preparation of intermediate:

5-methyl-6-(1H-3-methoxycarbonyl-1,4-dihydro-4-pyridinyl)-2H-1,4-thiazin-3(4H)-one Zinc powder (1.5 g) was added to a solution of 5-methyl-6-[1-(2,2,2-trichloroethoxycarbonyl)-3-methoxycarbonyl-1,4-dihydro-4-pyridinyl]-2H-1,4-thiazin-3(4H)-one (2.1 g) in 50% THF (60 ml) and the mixture was stirred at 60° C. for 2 hours and zinc powder (0.5 g) was added to the mixture gain and the mixture was stirred for further 2 hours. The reaction mixture was cooled to ambient temperature, was filtered and was washed with 50% THF. The filtrate was extracted with benzene. The extract was washed with water, was dried over magnesium sulfate and the solvent was removed under reduced pressure to give the titled compound (0.76 g, yield 60%) as pale yellow crystals.

Melting point: 176°–177° C.

IR spectrum $\nu_{max}^{KBr}$(cm$^{-1}$): 3200, 1620, 1600

MS spectrum: M$^+$266

NMR spectrum (DMSO-d$_6$, TMS, δ): 1.91 (3H, s), 3.05 (2H, ABq), 3.54 (3H, s), 4.39 (1H, d), 4.45 (1H, dd), 6.14 (1H, dd), 7.24 (1H, d), 8.30 (1H, s), 9.34 (1H, s)

(iii) preparation of 5-methyl-6-(3-methoxycarbonyl-4-pyridinyl)-2H:1,4-thiazin-3(4H)-one DDQ (0.65 g) was added to a solution of 5-methyl-6-(1H-3-methoxycarbonyl-1,4-dihydro-4-pyridinyl)-2H-1,4-thiazin-3(4H)-one (0.76 g) in dry acetonitrile (30 ml) and the mixture was stirred at 50° C. for 2 hours. The mixture was cooled to ambient temperature and was filtered. The solvent was removed under reduced pressure. The residue was chromatographed on silica gel (Wakogel C-200) column using chloroform-methanol (=20:1) as an eluant and was recrystallized from absolute ethanol to give the titled compound (0.48 g, yield 64%) as pale yellow crystals.

Melting point: 177°–178° C.

IR spectrum $\nu_{max}^{KBr}$(cm$^{-1}$): 3300, 1710, 1680, 1620

MS spectrum: M$^+$264

NMR spectrum (CDCl$_3$, TMS, δ): 1.83 (3H, s), 3.46 (2H, s), 3.94 (3H, s), 7.21 (1H, d), 8.33 (1H, s), 8.72 (1H, d), 9.12 (1H, s)

Example 7

(i) Preparation of intermediate:

5-methyl-6-[1-(2,2,2-trichloroethoxycarbonyl)-3-acetyl-1,4-dihydro-4-pyridinyl]-2H-1,4-thiazin -3(4H)-one A mixture of 3-acetylpyridine (2.18 ml), 2,2,2-trichloroethylchloroformate (3.44 ml) and 5-methyl-2H-1,4-thiazin-3(4H)-one (1.29 g) was treated in the same manner as described in Example 2 (i) to give the titled compound (1.77 g, yield 42%) as pale yellow crystals. Ethyl acetate-n-hexane (=1:1) was used as a developing eluant.

Melting point: 138°–140° C.

IR spectrum $\nu_{max}^{KBr}$(cm$^{-1}$): 3200, 3060, 2910, 1730, 1660

NMR spectrum (CDCl$_3$, TMS, δ):
2.13 (3H, s), 2.34 (3H, s), 3.12 (2H, ABq), 4.53 (1H, d), 4.86 (1H, m), 5.02 (2H, m), 7.00 (1H, d), 7.60 (1H, s), 8.03 (1H, s)

(ii) Preparation of
5-methyl-6-(3-acetyl-4-pyridinyl)-2H-1,4-thiazin-3(4H)-one

A mixture of 5-methyl-6-[1-(2,2,2-trichloroethoxycarbonyl)-3-acetyl-1,4-dihydro-4-pyridinyl]-2H-1,4-thiazin-3(4H)-one (1.77 g) and sulfur sublimed (0.8 g) was treated in the same manner as described in Example 3 (ii) to give the titled compound (0.08 g, yield 7.8%) as pale yellow crystals. Ethyl acetate was used as a developing eluant.

Melting point: 155°–157° C.
IR spectrum $\nu_{max}^{KBr}$(cm$^{-1}$): 3200, 1680, 1620
NMR spectrum (CDCl$_3$, TMS, δ): 1.84 (3H, s), 2.61 (3, s), 3.43 (2H, s), 7.23 (1H, d), 8.27 (1H, s), 8.69 (1H, d), 8.88 (1H, s)

Example 8

(i) Preparation of intermediate:

5-methyl-6-[1-(2,2,2-trichloroethoxycarbonyl)-6-methoxy-b 1,4-dihydro-4-quinolinyl]-2H-1,4-thiazin-3(4H)-one A mixture of 6-methoxyquinoline (1.1 ml), 2,2,2-trichloroethylchloroformate (1.4 ml) and 5-methyl-2H-1,4-thiazin-3(4H)-one (0.52 g) was treated in the same manner as described in Example 2 (i) to give the titled compound (0.6 g, yield 32%) as white crystals. n-Hexane-ethyl acetate (=3:2) was used as a developing eluant.

Melting point: 170°–171° C.
IR spectrum $\nu_{max}^{KBr}$(cm$^{-1}$): 3200, 3050, 2940, 1720, 1670
NMR spectrum (CDCl$_3$, TMS, δ): 2.13 (3H, s), 3.12 (2H, ABq), 3.79 (3H, s), 4.61 (1H, d), 4.92 (2H, s), 5.16 (1H, dd), 6.61 (1H, d), 6.84 (1H, dd), 7.20 (1H, d), 8.04 (1H, d), 8.06 (1H, s)

(ii) Preparation of
5-methyl-6-(6-methoxy-4-quinolinyl)-2H-1,4-thiazin-3(4H)-one A mixture of 5-methyl-6-[1-(2,2,2-trichlorethoxycarbonyl)-6-methoxy-1,4-dihydro-4-quinolinyl]-2H-1,4-thiazin-3(4H)-one (0.6 g) and sulfur sublimed (0.3 g) was treated in the same manner as described in Example 3 (ii) to give the titled compound (0.12 g, yield 33%) as pale red crystals. Ethyl acetate was used as a developing eluant.

Melting point: 178°–179°C.
IR spectrum $\nu_{max}^{KBr}$(cm$^{-1}$): 3200, 3100, 2950, 1680
NMR spectrum (CDCl$_3$, TMS, δ): 1.82 (3H, s), 3.55 (2H, ABq), 3.94 (3H, s), 7.15 (1H, d), 7.28 (1H, d), 7.41 (1H, dd), 8.06 (1H, d), 8.31 (1H, s), 8.78 (1H, d)

Example 9

(i) Preparation of intermediate:

5-methyl-6-[1-(2,2,2-trichloroethoxy-carbonyl)-3-methyl-1,4-dihydro-4-pyridazinyl]2H-1,4-thiazin-3(4H)-one A mixture of 3-methylpyridazine (1.82 ml), 2,2,2-trichloroethylchloroformate (3.44 ml) and 5-methyl-2H-1,4-thiazin-3(4H)-one (1.29 g) was treated in the same manner as described in Example 2 (i) to give the titled compound (0.4 g, yield 10%) as white crystals. n-Hexane-ethyl acetate (=3:2) was used as a developing eluant.

Melting point: 186°–187° C.
IR spectrum $\nu_{max}^{KBr}$(cm$^{-1}$): 3200, 3070, 2950, 1720, 1670, 1635
NMR spectrum (DMSO-d$_6$, TMS, δ): 1.92 (3H, s), 1.98 (3H, s), 3.08 (1H, d), 3.25 (1H, d), 4.20 (1H, d), 4.94 (1H, dd), 5.03 (2H, s), 7.17 (1H, d), 9.64 (1H, s)

(ii) Preparation of
5-methyl-6-(3-methyl-4-pyridazinyl)-2H-1,4-thiazin-3(4H)-one A mixture of 5-methyl-6-[1-(2,2,2-trichloroethoxycarbonyl)-3-methyl-1,4-dihydro-4-pyridazinyl]-2H-1,4-thiazin-3(4H)-one (0.4 g) and sulfur sublimed (0.2 g) was treated in the same manner as described in Example 3 (ii) to give the titled compound (0.08 g, yield 36%) as white crystals. Chloroform-methanol (=20:1) was used as a developing eluant.

Melting point: 186°–188° C.
IR spectrum $\nu_{max}^{KBr}$(cm$^{-1}$): 3200, 3050, 2900, 1670, 1620
NMR spectrum (CDCl$_3$, TMS, δ): 1.81 (3H, s), 2.75 (3H, s), 3.46 (2H, s), 7.26 (1H, d), 8.24 (1H, s), 9.09 (1H, d)

Example 10

(i) Preparation of intermediate:

5-methyl-6-[1-(2,2,2-trichloroethoxycarbonyl)-3-methyl-1,4-dihydro-4-pyridinyl]-2H-1,4-thiazin-3(4H)-one A mixture of 3-methylpyridine (0.72 g), 2,2,2-trichloroethylchloroformate (1.33 ml) and 5-methyl-2H-1,4-thiazin-3(4H)-one (0.5 g) was treated in the same manner as described in Example 2 (i) to give the titled compound (0.49 g, yield 31%) as milky white crystals. n-Hexane-ethyl acetate (=1:1) was used as a developing eluant.

Melting point: 149°–152° C.
IR spectrum $\nu_{max}^{KBr}$(cm$^{-1}$): 3190, 3070, 2930, 1720, 1670, 1630, 1380, 1320
NMR spectrum (CDCl$_3$, TMS, δ): 1.65 (3H, s), 2.03 (3H, s), 3.21 (2H, ABq), 4.02 (1H, d), 4.74–4.96 (2H+1H, m), 6.80 (1H, d), 6.98 (1H, d), 8.04 (1H, s)

(ii) Preparation of
5-methyl-6-(3-methyl-4-pyridinyl)-2H-1,4-thiazin-3(4H)-one

A mixture of 5-methyl-6-[1-(2,2,2-trichloroethoxycarbonyl)-3-methyl-1,4-dihydro-4-pyridinyl]-2H-1,4-thiazin-3(4H)-one (0.25 g) and sulfur sublimed (0.125 g) was treated in the same manner as described in Example 3 (ii) to give the titled compound (0.118 g, yield 86.3%) as pale brown crystals. Chloroform-methanol (=20:1) was used as a developing eluant.

Melting point: 185°–187° C.
IR spectrum $\nu_{max}^{KBr}$(cm$^{-1}$): 3040, 2850, 1670, 1630, 1590, 1330
NMR spectrum (CDCl$_3$, TMS, δ): 1.78 (3H, s), 2.31 (3H, s), 3.44 (2H, s), 7.09 (1H, d), 8.44 (1H, d), 8.51 (1H, s), 8.58 (1H, s)

Example 11

(i) Preparation of intermediate:

5-methyl-6-(3-ethoxycarbonyl-dihydro-2-thiazolyl)-2H-1,4-thiazin-3(4H)-one

Ethylchloroformate (3.6 g) was added dropwise to a solution of thiazole (5.7 g) in dichloromethane (72 ml) under ice-cooling, and the mixture was stirred for 30 minutes. Then, 5-methyl-2H-1,4-thiazin-3(4H)-one (3.6 g) was added dropwise to the mixture. The reaction mixture was further stirred at ambient temperature for 5 hours. The mixture was washed with 2N hydrochloric acid and successively with water, was dried over anhydrous magnesium sulfate and the solvent was removed. The residue was chromatographed on silica gel (Wakogel C-200) column, using ethyl acetate-n-hexane (=1:1) as an eluant and was recrystallized from ethanol to give the titled compound (1.9 g, yield 23.8%) as white needles.

Melting point: 146°–147° C.

IR spectrum $\nu_{max}^{KBr}$(cm$^{-1}$): 3220, 3130, 1700, 1680, 1640, 1600

(ii) Preparation of
5-methyl-6-(2-thiazolyl)-2H-1,4-thiazin-3(4H)-one

DDQ (0.16 g) was added to 5-methyl-6-(3-ethoxycarbonyl-dihydro-2-thiazolyl)-2H-1,4-thiazin-3(4H)-one (0.2 g) in dichloromethane (5 ml) and the reaction mixture was stirred at ambient temperature for 1.5 hours. The resulting crystals were filtrated, were washed with saturated aqueous calcium bicarbonate and successively with water, was recrystallized from methanol to give the titled compound (0.08 g, yield 54.0%) as white needles.

Melting point: 233°–235° C. (decomposition)

IR spectrum $\nu_{max}^{KBr}$(cm$^{-1}$): 3200, 3080, 1680, 1615

NMR spectrum (DMSO-d$_6$, TMS, δ): 2.4 (3H, s), 3.4 (2H, s), 7.7 (1H, d), 7.9 (1H, d), 10.2 (1H, s)

Example 12

(i) Preparation of intermediate:
ethyl thiolactate

Conc. sulfuric acid (2 ml) was added as catalyst to a stirred solution of thiolactic acid (25 g) in absolute ethanol (200 ml) and the solution was refluxed for 6 hours. After conclusion of reaction was checked by gas chromatography [column:FFAP, column temperature 100° C., carrier gas N$_2$ (20 ml/min)], ethanol was removed at atmospheric pressure. The resulting solution was distillated under reduced pressure to give the titled oily compound (19.1 g, yield 58%).

Boiling point: 52°–54° C./16 mmHg

NMR spectrum (CDCl$_3$, TMS, δ): 1.29 (3H, t), 1.54 (3H, d), 2.16 (1H, d), 3.53 (1H, m), 4.20 (2H, q)

(ii) Preparation of intermediate:
2,5-dimethyl-2H-1,4-thiazin-3(4H)-one

Ethyl thiolactate (19.0 g) was added to aqueous ammonia (100 ml) and the mixture was stirred under nitrogen atmosphere at ambient temperature for 20 hours. The solvent was removed under reduced pressure and the residue was ice-cooled to give thiolacticamide as white crystals.

These crystals are dissolved in absolute ethanol (100 ml) and added with triethylamine (20 ml). A solution (40 ml) of chloroacetone (12 ml) in ether was added dropwise to the mixture over about 2 hours under ice-cooling. The reaction mixture was further stirred for 2 hours at ambient temperature. The solvent was removed under reduced pressure at 50° C. and the residue was added with acetone (150 ml) and was filtered. The filtrate was concentrated under reduced pressure and was added with absolute ethanol (100 ml), was adjusted to pH 1–2 by p-toluenesulfonic acid, and was heated to 60°–70° C. for 30 minutes, and the solvent was removed under reduced pressure. The residue was chromatographed on silica gel (Wakogel C-200) column, using ethyl acetate-n-hexane (=1:1) as an eluant to give the titled compound (3.9 g, yield 11%) as white crystals.

Melting point: 78°–80° C.

Elementary analysis values as: C$_6$H$_9$NOS; Calculated: C=50.32; H=6.33; N=9.78 (%); Found: C=50.06; H=6.47; N=9.62 (%)

IR spectrum $\nu_{max}^{KBr}$(cm$^{-1}$): 3200, 3100, 1670, 1630

NMR spectrum (CDC$_3$, TMS, δ): 1.44 (3H,d), 1.95 (3H, s), 3.35 (1H, dd), 5.21 (1H, s), 8.07 (1H, s)

(iii) Preparation of intermediate:
2,5-dimethyl-6-[1-(2,2,2-trichloroethoxycarbonyl)-1,4-dihydro-4-pyridinyl]-2H-1,4-thiazin-3(4H)-one 2,2,2-Trichloroethylchloroformate (1.68 ml) was added dropwise to a solution of 2,5-dimethyl-2H-1,4-thiazin-3(4H)-one (1.43 g) and pyridine (1.6 ml) in acetonitrile (50 ml) under ice-cooling, and the solution was stirred for 30 minutes at 0° C. The mixture was further stirred at ambient temperature for 2 hours. The solvent was removed under reduced pressure. The residue was extracted with chloroform, was washed with 2N hydrochloric acid and successively with water and was dried over magnesium sulfate. The solvent was removed and the residue was chromatographed on silica gel (Wakogel C-200) column, using ethyl acetate-n-hexane (=1:1) as an eluant. The eluate was washed with ether to give the titled compound (1.68 g, yield 42%) as pale yellow crystals.

Melting point: 140°–142° C.

Elementary analysis values as: C$_{14}$H$_{15}$N$_2$O$_3$SCl$_3$; Calculated: C=42.28; H=3.80; N=7.04 (%); Found: C=42.33; H=3.89; N=7.17 (%)

IR spectrum $\nu_{max}^{KBr}$(cm$^{-1}$): 3200, 3080, 2950, 1720, 1670, 1630

NMR spectrum (CDCl$_3$, TMS, δ): 1.40 (3H, d), 1.98 (3H, s), 3.33 (1H, q), 4.16 (1H, m), 4.77 (2H, d), 4.92 (2H, d), 6.95 (2H, d), 7.75 (1H, s)

(iv) Preparation of
2,5-dimethyl-6-(4-pyridinyl)-2H-1,4-thiazin-3(4H)-one

Sulfur sublimed (0.7 g) was added to a solution of 2,5-dimethyl-6-[1-(2,2,2-trichloroethoxycarbonyl)-1,4-dihydro-4-pyridinyl]-2H-1,4-thiazin-3(4H)-one (1.5 g) in dimethylformamide (20 ml) and the mixture was stirred at 140° C. for 2 hours. Then, the mixture was allowed to cool to ambient temperature and the solvent was removed under reduced pressure. The residue was dissolved in 2N hydrochloric acid and the insoluble matter was removed by filtration. The filtrate was adjusted to pH 7–8 by 2N aqueous sodium hydroxide. The precipitated crude crystals were chromatographed on silica gel (Wakogel C-200) column, using chloroform-methanol (=20:1) as an eluant to give pale yellow crystals. These crude crystals were dissolved in chloroform, were washed with water and were dried over magnesium sulfate. The solvent was removed under reduced pressure to give the titled compound (0.43 g, yield 52%) as white crystals.

Melting point: 144°–146° C.

Elementary analysis values as: C$_{11}$H$_{12}$N$_2$OS; Calculated: C=59.97; H=5.49; N=12.71 (%); Found: C=59.76; H=5.55; N=12.55; (%)

IR spectrum $\nu_{max}^{KBr}$(cm$^{-1}$): 3200, 3090, 2950, 1680, 1620

NMR spectrum (CDCl$_3$, TMS, δ): 1.53 (3H, d), 2.05 (3H, s), 3.53 (1H, q), 7.28 (2H, dd), 7.40 (1H, s), 8.61 (2H, dx2)

Example 13

(i) Preparation of intermediate:

δ-bromo-n-butylamide

δ-Bromo-n-butylbromide (9.7 ml) was slowly added dropwise to a conc. aqueous ammonia (28%, 33 ml) at less than −10° C. while being stirred violently. The precipitated white crystals were suspended in water, were extracted with ethyl acetate. The extract was washed with water, was dried over magnesium sulfate. The solvent was removed under reduced pressure to give the titled compound (9.57 g, yield 72%) as white crystals.

Melting point: 109°–111° C.

IR spectrum $\nu_{max}^{KBr}$(cm$^{-1}$): 3360, 3180, 1670

NMR spectrum (CDCl$_3$, TMS, δ): 1.03 (3H, t), 2.13 (2H, m), 4.30 (1H, t), 6.50 (2H, s)

(ii) Preparation of intermediate:

2-ethyl-5-methyl-2H-1,4-thiazin-3(4H)-one

α-Bromo-n-butylamide (1.66 g) and potassium xanthogenate (1.60 g) were suspended in acetone (20 ml) and the suspension was stirred at ambient temperature for 2 hours, then the mixture was filtered. The filtrate was condenced to give oily product. Benzen (15 ml) and morphorine (1.7 ml) were added to the oily product. The mixture was refluxed for 2 hours under heating and was allowed to cool. The solvent was removed under reduced pressure to give α-mercapto-n-butylamide. Without purification, this amide is added with absolute ethanol (15 ml) and triethylamine (1.3 ml) and then chloroacetone (0.8 ml) in ether (1.0 ml) was added dropwise to the solution under ice-cooling for 2 hours. Then, the reaction mixture was stirred at ambient temperature for overnight. The solvent was removed under reduced pressure to give oily product. Acetone (20 ml) was added to the oily product and the mixture was filtered for removal of the precipitated crystals. Further, the crystals were washed with acetone (10 ml) and the mother liquor was condenced, was added with absolute ethanol (10 ml), was adjusted to pH 1–2 by p-toluenesulfonic acid, was heated at 70° C. for 30 minutes. The solvent was removed under reduced pressure and the residue was extracted with ethyl acetate. The extract was washed with water, was dried over magnesium sulfate, and the solvent was removed under reduced pressure. The residue was chromatographed on silica gel (Wakogel C-200) column, using ethyl acetate-n-hexane (=1:3) as an eluant to give the titled compound (1.21 g, yield 77%) as white crystals.

Melting point: 69°–71° C.

Elementary analysis values as: C$_7$H$_{11}$NOS; Calculated: C=53.47; H=7.05; N=8.90 (%); Found: C=53.51; H=7.28; N=8.86 (%);

IR spectrum $\nu_{max}^{KBr}$(cm$^{-1}$): 3200, 3100, 2950, 1680

NMR spectrum (CDCl$_3$, TMS, δ): 1.04 (3H, dd), 1.65 (1H, m), 1.90 (1H, m), 1.93 (3H, s), 3.12 (1H, m), 5.14 (1H, s), 7.92 (1H, s)

(iii) Preparation of
2-ethyl-5-methyl-6-(4-pyridinyl)-2H-1,4-thiazin-3(4H)-one 2,2,2-Trichloroethylchloroformate (1.0 ml) was added dropwise to a solution of 2-ethyl-5-methyl-2H-1,4-thiazin-3(4H)-one (0.94 g) and pyridine (0.96 ml) in acetonitrile (30 ml) under ice-cooling, and the mixture was stirred at 0° C. for 30 minutes. Then the mixture was further stirred at ambient temperature for 18 hours. The solvent was removed under reduced pressure and the residue was extracted with ethyl acetate, was washed with water, 2N hydrochloric acid and water in the order named, and was dried over magnesium sulfate. The solvent was removed under reduced pressure to give 2-ethyl-5-methyl-6-[1-(2,2,2-trichloroethoxycarbonyl)-1,4-dihydro-4-pyridinyl]-2H-1,4-thiazin-3(4H)-one (2.0 g) as pale yellow oily product.

This oily product was dissolved in dimethylformamide (20 ml), was added with sulfur sublimed (0.6 g) and was stirred at 140° C. for 3 hours. The mixture was allowed to cool and the solvent was removed under reduced pressure. The residue was dissolved in 2N hydrochloric acid. The insoluble matter was removed by filtration and the filtrate was washed with ether and the water phase was adjusted to neutralization by 2N aqueous sodium hydroxide, was extracted with chloroform. The extract was washed with water and was dried over magnsium sulfate. The solvent was removed under reduced pressure and the residue was chromatographed on silica gel (Wakogel C-200) column, using chloroform-methanol (=20:1) as an eluant. The eluate was recrystallized from aqueous solution of 30% ethanol to give the titled compound (0.3 g, yield 21%) as pale yellow crystals.

Melting point: 121°–123° C.

IR spectrum $\nu_{max}^{KBr}$(cm$^1$): 3210, 3100, 2960, 1670

NMR spectrum (CDCl$_3$, TMS, δ): 1.14 (3H, t), 1.76 (1H, m), 1.99 (1H, m), 3.28 (1H, dd), 7.27 (2H, dd), 8.52 (1H, s), 8.61 (2H, dx2)

Example 14

(i) Preparation of intermediate:

5-methyl-6-[1-(2,2,2-trichloroethoxycarbonyl)-1,4-dihydro-4-pyridinyl]-2H-1,4-thiazin-3(4H)-one 2,2,2-Trichloroethylchloroformate (64 ml) was added dropwise to a suspension of 5-methyl-2H-1,4-thiazin-3(4H)-one (50 g) and acetonitrile (500 ml) in pyridine (75 ml) under ice/water-cooling. The reaction mixture was further stirred at ambient temperature for 1 hour. Then, the mixture was added with ice water (about 1.5 l), was stirred for a while and was filtered. The filtration was recrystallized from ethanol to give the titled compound (120 g, yield 80.7%) as pale yellow prisms.

Melting point: 158°–160° C.

Elementary analysis values as: C$_{13}$H$_{13}$N$_2$O$_3$SCl$_3$; Calculated: C=40.69, H=3.41; N=7.29 (%); Found: C=40.62; H=3.37; N=7.02 (%)

IR spectrum $\nu_{max}^{KBr}$(cm$^{-1}$): 3200, 3100, 1720, 1670, 1630

MS spectrum: M+382

NMR spectrum (CDCl$_3$, TMS, δ): 1.986 (3H, s), 3.229 (2H, s), 4.161 (1H, m), 4.800 (4H, m), 6.970 (2H, d), 7.264 (1H, b)

(ii) Preparation of
5-methyl-6-(4-pyridinyl)-2H-1,4-thiazin-3(4H)-one 5-methyl-6-[1-(2,2,2-trichloroethoxycarbonyl)-1,4-dihydro-4-pyridinyl]-2H-1,4-thiazin-3(4H)-one (2.14 g) was mixed well with sulfur sublimed (10.7 g) in a mortar and the mixture was stirred at 140° C. for 1.5 hours. Then, the mixture was cooled to ambient temperature. The obtained solid was ground and was extracted with methanol using Soxhlet extractor. Methanol was removed under reduced pressure. The residue was dissolved in 50 ml of 2N hydrochloric acid. The insoluble matter was removed by filtration and the filtrate was adjusted to pH 7.2 by 2N aqueous sodium hydroxide. The resulting precipitates were collected by filtration and the filtrate was extracted with chloroform (20 ml×5 times) and was evaporated to dryness. After combined with the above solid, the residue was recrystallized from isopropanol to give the titled compound (0.88 g, yield 76.5%) as pale yellow plates.

Melting point: 187°–188.5° C.

Elementary analysis values as: $C_{10}H_{10}N_2OS$; Calculated: C=58.22; H=4.88; N=13.58 (%); Found: C=58.48; H=4.99; N=13.53 (%)

IR spectrum $\nu_{max}^{KBr}(cm^{-1})$: 3200, 3050, 1680, 1580

MS spectrum: M+206

NMR spectrum (CDCl$_3$, TMS, δ): 2.056 (3H, s), 3.437 (2H, s), 7.280 (2H, d), 8.610 (2H, d), 8.700 (1H, d)

Example 15

Preparation of 2-methoxy-5-methyl-6-(4-pyridinyl)-2H-1,4-thiazin-3(4H)-one m-Chloroperbenzoic acid (12 g) was added gradually to a stirred suspension of 5-methyl-6-(4-pyridinyl)-2H-1,4-thiazin-3(4H)-one (10 g) in methanol (400 ml) under ice/water-cooling. The reaction mixture was further stirred at ambient temperature for 3 days. The solvent was removed under reduced pressure and the residue was extracted with ethyl acetate, was washed with saturated sodium bicarbonate aqueous solution and successively with water and was dried over magnesium sulfate. The solvent was removed under reduced pressure and the residue was dissolved in chloroform (about 50 ml) and was chromatographed on activated alumina (200 g, about 300 mesh, manufactured by Wako Pure Chemical Industries, Ltd.) cloumn, using chloroform as an eluant. The solvent was removed under reduced pressure and the residue was crystallized from ether to give the titled compound (6 g, yield 51.7%) as pale yellow powder.

Melting point: 133.5°–135° C.

IR spectrum $\nu_{max}^{KBr}(cm^{-1})$: 3200, 3050, 1690, 1610, 1590

NMR spectrum (CDCl$_3$, TMS, δ): 2.07 (3H, s), 3.55 (3H, s), 4.90 (1H, s), 7.27 (2H, dd), 8.62 (2H, dx2) 9.10 (1H, s)

Example 16

Preparation of 2,2-dimethoxy-5-methyl-6-(4-pyridinyl)-2H-1,4-thiazin-3(4H)-one m-Chloroperbenzoic acid (2.8 g) was added to a stirred solution of 2-methoxy-5-methyl-6-(4-pyridinyl)-2H-1,4-thiazin-3(4H)-one (2.7 g) in methanol (100 ml) under ice/water-cooling. The reaction mixture was further stirred at ambient temperature for 2 hours. Methanol was removed under reduced pressure and the residue was dissolved in ethyl acetate, was washed with saturated sodium bicarbonate aqueous solution and successively with water, and was dried over magnesium sulfate. Ethyl acetate was removed under reduced pressure and the residue was crystallized from ether to give the titled compound (2 g, yield 66.7%) as pale yellow powder.

Melting point: 154°–155° C.

NMR spectrum (CDCl$_3$, TMS, δ): 2.03 (3H, s), 3.59 (6H, s), 7.25 (2H, dd), 8.43 (1H, s), 8.62 (2H, dx2)

Example 17

(i) Preparation of 5-methyl-6-(4-pyridinyl)-2H-1,4-thiazin-3(4H)-one

Zinc powder (1.7 g) was added to a solution of 5-methyl-6-[1-(2,2,2-trichloroethoxycarbonyl)-1,4-dihydro-4-pyridinyl]-2H-1,4-thiazin-3(4H)-one (1g) in formic acid (14 ml) and the mixture was stirred at ambient temperature for 3 hours. The mixture was filtered and the filtrate was evaporated to dryness. The residue was dissolved in water (30 ml), was adjusted to pH 7.0 by 1N aqueous sodium hydroxide, was extracted with chloroform and was dried over magnesium sulfate. Chloroform was removed and the residue was purified by the preparative thin layer chromatography [Merck TLC plate, silica gel 60F$_{254}$ (supplied by Merck & Co. Inc., U.S.A.), 20×20 cm, thickness=1 mm, developing solvent; chloroform/methanol=20:1] to give the titled compound (0.2 g, yield 37.1%) as pale yellow plates. The physiocochemical properties were as described above.

(ii) Preparation of intermediate:

2-(3-chlorobenzoyloxy)-5-methyl-6-(4-pyridinyl)-2H-1,4-thiazin-3(4H)-one m-Chloroperbenzoic acid (8.97 g, 70% purity) was added to a solution of 5-methyl-6-(4-pyridinyl)-2H-1,4-thiazin-3(4H)-one (5.0 g) in dichloromethane (120 ml) under ice/water-cooling and the mixture was stirred for 10 minutes under ice/water-cooling. The mixture was washed with saturated sodium bicarbonate aqueous solution (2 times) and successively with water (1 time) and was dried over magnsium sulfate. The solvent was removed under reduced pressure and the residue was recrystallized from ether-petrolem ether to give the titled compound (3.29 g, yield 37.6%) as pale yellow needles.

Melting point: 142°–143° C.

IR spectrum $\nu_{max}^{KBr}(cm^{-1})$: 3180, 3080, 2920, 1720, 1670, 1620, 1590

NMR spectrum (CDCl$_3$, TMS, δ): 2.19 (3H, s), 6.60 (1H, s), 7.28 (2H, dd), 7.47–8.23 (4H, m), 8.69 (2H, dx2), 9.78 (1H, s)

(iii) Preparation of 2-amino-5-methyl-6-(4-pyridinyl)-2H-1,4-thiazin-3(4H)-one

Ammonium carbonate (0.6 g) was added to a solution of 2-(3-chlorobenzoyloxy)-5-methyl-6-(4-pyridinyl)-2H-1,4-thiazin-3(4H)-one (0.4 g) in acetonitrile (20 ml). The mixture was stirred at ambient temperature for 3 days, was filtered and the filtrate was evaporated to dryness. The residue was chromatographed on silica gel (Wakogel C-200) column, using chloroform-methanol (=20:1) as an eluant to give the titled compound (0.1 g, yield 40.7%).

IR spectrum $\nu_{max}^{KBr}(cm^{-1})$: 3370, 3300, 3200, 3060, 1665, 1610, 1580

NMR spectrum (CDCl$_3$, TMS, δ): 2.70 (5H, s), 4.68 (1H, s), 7.28 (2H, dd), 8.55 (1H, s), 8.62 (2H, dx2)

p-Toluenesulfonic acid hydrate (0.19 g) was added to a solution of the titled compound in methanol (10 ml) and the mixture was stirred at ambient temperature for 0.5 hour. Methanol is removed under reduced pressure and the residue was crystallized from acetone to give p-tosylate as pale yellow powder.

Melting point: 213°–217° C. (decomposition)

Example 18

Preparation of 2-diethylamino-5-methyl-6-(4-pyridinyl)-2H-1,4-thiazin-3(4H)-one hydrochloride Diethylamine (2.58 ml) was added to a solution of 2-(3-chlorobenzoyloxy)-5-methyl-6-(4-pyridinyl)-2H-1,4-thiazin-3(4H)-one (0.9 g) in dry dichloromethane (12 ml) and the mixture was stirred at ambient temperature for 21 hours. The solvent was removed under reduced pressure and the residue was dissolved in ethyl acetate, was washed with saturated sodium bicarbonate aqueous solution and successively with water and was dried over magnesium sulfate. The solvent was removed under reduced pressure and the residue was chromatographed on silica gel (Wakogel C-200) column, using chloroform-methanol (=20:1) as an eluant to give pale yellow oily product. The oily product was dissolved in methanol and was adjusted to pH 2 by 2N hydrochloric acid. The solvent was removed under reduced pressure and the residue was washed with THF and allowed to stand to give the titled compound (0.685 g, yield 78.4%) as yellow crystals.

Melting point: over 240° C. (decomposition)

IR spectrum $\nu_{max}^{KBr}$(cm$^{-1}$): 3050, 2890, 2420, 2070, 1680, 1605

NMR spectrum (DMSO-d$_6$, TMS, δ): 1.21 (6H, m), 2.10 (3H, s), 3.08 (4H, m), 5.37 (1H, s), 8.08 (2H, d), 8.86 (2H, d), 11.10 (1H, s)

Example 19 to Example 22 were treated in the same manner as described in Example 18.

Example 19

Preparation of 5-methyl-2-methylamino-6-(4-pyridinyl)-2H-1,4-thiazin-3(4H)-one 2-(3-Chlorobenzoyloxy)-5-methyl-6-(4-pyridinyl)-2H-1,4-thiazin-3(4H)-one and methylamine were reacted to give the titled compound as pale brown needles.

Melting point: 170°–172° C. (decomposition)

IR spectrum $\nu_{max}^{KBr}$(cm$^{-1}$): 3310, 3220, 3090, 2940, 2800, 1690, 1640, 1600

NMR spectrum (CDCl$_3$, TMS, δ): 1.82 (1H, s), 2.08 (3H, s), 2.62 (3H, s), 4.43 (1H, s), 7.25 (2H, dd), 8.62 (2H, dx2), 9.21 (1H, s)

Example 20

Preparation of 5-methyl-2-morphorino-6-(4-pyridinyl)-2H-1,4-thiazin-3(4H)-one 2-(3-Chlorobenzoyloxy)-5-methyl-6-(4-pyridinyl)-2H-1,4-thiazin-3(4H)-one and morphorine were reacted to give the titled compound as pale brown crystals.

Melting point: 166°–167° C.

IR spectrum $\nu_{max}^{KBr}$(cm$^{-1}$): 3225, 3075, 2860, 2840, 1690, 1645, 1625

NMR spectrum (CDCl$_3$, TMS, δ): 2.03 (3H, s), 2.57–2.93 (4H, m), 3.77 (4H, t), 4.64 (1H, s), 7.31 (2H, dd), 8.64 (2H, dx2), 9.83 (1H, s)

Example 21

Preparation of 5-methyl-2-piperidino-6-(4-pyridinyl)-2H-1,4-thiazin-3(4H)-one hydrochloride 2-(3-Chlorobenzoyloxy)-5-methyl-6-(4-pyridinyl)-2H-1,4-thiazin-3(4H)-one and piperidine were reacted. The resultant compound was added with hydrochloric acid and was recrystallized from ethanol to give the titled compound as yellowish brown crystals.

Melting point: 228.5° C. (decomposition)

IR spectrum $\nu_{max}^{KBr}$(cm$^{-1}$): 3040, 2925, 2880, 2475, 2070, 1980, 1850, 1680, 1620

NMR spectrum (DMSO-d$_6$, TMS, δ): 1.47 (2H, m), 1.72 (4H, m), 2.09 (3H, s), 2.78–3.12 (4H, m), 5.23 (1H, s), 8.06 (2H, dd), 8.85 (2H, dx2), 10.98 (1H, s)

Example 22

Preparation of 5-methyl-2-phenylamino-6-(4-pyridinyl)-2H-1,4-thiazin-3(4H)-one 2-(3-Chlorobenzoyloxy)-5-methyl-6-(4-pyridinyl)-2H-1,4-thiazin-3(4H)-one and aniline were reacted to give the titled compound as pale yellow crystals.

Melting point: 162°–165° C.

IR spectrum $\nu_{max}^{KBr}$(cm$^{-1}$): 3400, 3270, 3050, 2850, 2720, 1690, 1625, 1600

NMR spectrum (DMSO-d$_6$, TMS, δ): 2.00 (3H, s), 5.37 (1H, d), 6.38 (1H, d), 6.68–7.17 (5H, m), 7.20 (2H, dd), 8.50 (2H, dx2), 10.25 (1H, s)

Example 23

Preparation of 2-hydroxy-5-methyl-6-(4-pyridinyl)-2H-1,4-thiazin-3(4H)-one (i) 2-(3-Chlorobenzoyloxy)-5-methyl-6-(4-pyridinyl)-2H-1,4-thiazin-3(4H)-one (1.37 g) and water (1 ml) were dissolved in acetone (20 ml) and the mixture was stirred at 70° C. for 44 hours. The mixture was chromatographed on silica gel (Wakogel C-200) column, using chloroform-methanol (=30:1) as an eluant to give the titled compound (0.16 g, yield 19.1%) as red needles.

Melting point: 214°–214.5° C.

IR spectrum $\nu_{max}^{KBr}$(cm$^{-1}$): 3430, 3180, 3030, 2920, 1660, 1610, 1580

MS spectrum: M+222

NMR spectrum (DMSO-d$_6$, TMS, δ): 1.94 (3H, s), 5.13 (1H, d), 6.93 (1H, d), 7.33 (2H, dd), 8.55 (2H, dx2), 10.11 (1H, s)

(ii) m-Chloroperbenzoic acid (0.216 g) was added to 5-methyl-2H-1,4-thiazin-3(4H)-one (0.129 g) in dry acetone (4 ml) under ice-cooling and the mixture was stirred for 2 hours. Water was added to the mixture and the solution was stirred for 30 minutes. Then, the reaction mixture was further stirred at ambient temperature for 3 hours. The solvent was removed under reduced pressure and the residue was chromatographed on silica gel (Wakogel C-200) column, using ethyl acetate-n-hexane (=2:1) as an eluant to give 2-hydroxy-5-methyl-2H-1,4-thiazin-3(4H)-one (0.068 g, yield 46.9%) as white crystals.

Melting point: 166.5°–168° C.

IR spectrum $\nu_{max}^{KBr}$(cm$^{-1}$): 3260, 3190, 3080, 2950, 1655, 1635

NMR spectrum (DMSO-d$_6$, TMS, δ): 1.86 (3H, s), 4.96 (1H, d), 5.20 (1H, s), 6.62 (1H, d), 9.77 (1H, s)

A mixture of pyridine, 2,2,2-trichloroethylchloroformate and 2-hydroxy-5-methyl-2H-1,4-thiazin-3(4H)-one was treated in the same manner as described in Example 6. The residue was recrystallized from ethanol to give the titled compound as pale yellow crystals.

Example 24

Preparation of 2-(4-hydroxyphenyl)-5-methyl-6-(4-pyridinyl)-2H-1,4-thiazin-3(4H)-one Silica gel (Wakogel C-200, 40 mg) was added as catalyst to a solution of 2-(3-chlorobenzoyloxy)-5-methyl-6-(4-pyridinyl)-2H-1,4-thiazin-3(4H)-one (0.98 g) and phenol (0.51 g) in acetonitrile (20 ml) and the mixture was stirred at 50° C. for 35 hours. The mixture was chromatographed on silica gel (Wakogel C-200) column, using chloroform-acetonitrile (=5:1) as an eluant. The residue was recrystallized from ethanol to give the titled compound (0.19 g, yield 23.4%) as pale yellow powder.

Melting point: 198°–200° C.

IR spectrum $\nu_{max}^{KBr}$(cm$^{-1}$): 3380, 3190, 3050, 3400, 1660, 1620, 1590

NMR spectrum (DMSO-d$_6$, TMS, δ): 2.01 (3H, s), 4.82 (1H, s), 6.76–7.18 (4H, m), 7.13 (2H, dd), 8.49 (2H, dx2), 9.95 (1H, s), 10.36 (1H, s)

Example 25

Preparation of 2-(2-furyl)-5-methyl-6-(4-pyridinyl)-2H-1,4-thiazin-3(4H)-one

Silica gel (Wakogel C-200, 0.03 g) was added as catalyst to a solution of 2-(3-chlorobenzoyloxy)-5-methyl-6-(4-pyridinyl)-2H-1,4-thiazin-3(4H)-one (0.79 g) and furan (0.30 g) in acetonitrile (30 ml) and the mixture was stirred at 50° C. for 35 hours. The mixture was chromatographed on silica gel (Wakogel C-200) column, using acetonitrile as an eluant. The residue was recrystallized from acetonitrile to give the titled compound (0.23 g, yield 37.7%) as pale orange crystals.

Melting point: 178°–179.5° C.

IR spectrum $\nu_{max}^{KBr}$(cm$^{-1}$): 3030, 2820, 1650, 1590, 1330

NMR spectrum (CDCl$_3$, TMS, δ): 2.04 (3H, s), 4.72 (1H, s), 6.30 (1H, d), 6.37 (1H, t), 7.14 (2H, dd), 7.44 (1H, d), 8.18 (1H, s), 8.57 (2H, dx2)

CAPABILITY OF EXPLOITATION IN INDUSTRY

As is apparent from the foregoing description, the novel 1,4-thiazine derivative of the present invention is a compound not described in any literature, capable of increasing contractile force of cardiac muscle and having low acute toxicity so that it is effective in curing and preventing heart diseases.

The process for preparation of the 1,4-thiazine derivative according to the present invention is advantageous from the industrial viewpoint because it may be prepared from relatively easily available starting compounds in high yield by a relatively easy operation.

What is claimed is:

1. A 1,4-thiazine derivative represented by the formula I and pharmaceutically acceptable acid addition salt thereof:

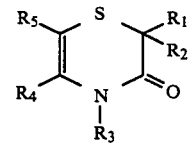

wherein
R$_1$ and R$_2$ represent respectively hydrogen atom, lower alkyl group, lower alkoxy group, unsubstituted amino group, lower alkyl-amino group, aryl-amino group, wherein the aryl-amino is one of phenyl-amino, tolyl-amino, xylyl-amino, mesitylamino, cumenyl-amino or biphenyl-amino which may be unsubstituted or may be substituted with lower alkyl, lower alkoxy, halogeno, aldehyde, acyl, cyano, nitro or hydroxy, hydroxy group, aryl group wherein the aryl is one of phenyl, tolyl, xylyl, mesityl, cumenyl or biphenyl which may be unsubstituted or may be substituted with lower alkyl, lower alkoxy, halogeno, aldehyde, acyl, cyano, nitro or hydroxy, or 5- or 6-membered heterocyclic residue; wherein the residue is furyl, thienyl, pyrrolyl, pyrano, pyridinyl, pyridazino, pyrimidino, piperidino, piperazino or morpholino;

R$_3$ and R$_4$ represent hydrogen atom or lower alkyl group; and

R$_5$ represents N-containing heterocyclic residue wherein said residue is one of pyridinyl, pyridazinyl, pyrimidinyl, pyrazinyl, quinolinyl, iso-quinolinyl, cinnolinyl, quinazolinyl, quinoxalinyl, phthalazainyl, acridinyl, thiazolyl, piperidinyl, piperazinyl or morpholinyl which may be unsubstituted or may be substituted with lower alkyl, lower alkoxy, halogeno, aldehyde, acyl, cyano, nitro, hydroxy or lower alkoxycarbonyl, and is not pyridinyl group when R$_1$ and R$_2$ represent hydrogen atom and R$_3$ and R$_4$ represent hydrogen atom or lower alkyl group.

2. 1.4-thiazine derivative represented by the formula I and pharmaceutically acceptable acid addition salt thereof according to claim 1 wherein R$_1$ and R$_2$ are hydrogen atom.

3. A 1,4-thiazine derivative represented by the formula I and pharmaceutically acceptable acid addition salt thereof according to claim 1 wherein R$_1$ and R$_2$ are methyl group or ethyl group.

4. A 1,4-thiazine derivative represented by the formula I and pharmaceutically acceptable acid addition salt thereof according to claim 1 wherein R$_1$ and R$_2$ are amino group.

5. A 1,4-thiazine derivative represented by the formula I and pharmaceutically acceptable acid addition salt thereof according to claim 1 wherein R$_1$ and R$_2$ are methylamino group or diethylamino group.

6. A 1,4-thiazine derivative represented by the formula I and pharmaceutically acceptable acid addition salt thereof according to claim 1 wherein R$_1$ and R$_2$ are phenylamino group.

7. A 1,4-thiazine derivative represented by the formula I and pharmaceutically acceptable acid addition salt thereof according to claim 1 wherein R$_1$ and R$_2$ are hydroxy group.

8. A 1,4-thiazine derivative represented by the formula I and pharmaceutically acceptable acid addition salt thereof according to claim 1 wherein $R_1$ and $R_2$ are phenyl group or hydroxyphenyl group.

9. A 1,4-thiazine derivative represented by the formula I and pharmaceutically acceptable acid addition salt thereof according to claim 1 wherein $R_1$ and $R_2$ are a furyl group, piperidino group or morphorino group.

10. A 1,4-thiazine derivative represented by the formula I and pharmaceutically acceptable acid addition salt thereof according to claim 1 wherein $R_3$ is hydrogen atom.

11. A 1,4-thiazine derivative represented by the formula I and pharmaceutically acceptable acid addition salt thereof according to claim 1 wherein $R_4$ is methyl group.

12. A 1,4-thiazine derivative represented by the formula I and pharmaceutically acceptable acid addition salt thereof according to claim 1 wherein $R_5$ is pyridinyl, pyridazinyl, quinolinyl, thiazolyl, methylpyridinyl, chloropyridinyl, formylpyridinyl, cyanopyridinyl, acetylpyridinyl, methoxyquinolinyl, methylpyridazinyl or methoxycarbonylpyridinyl.

13. A 1,4-thiazine derivative represented by the formula I and pharmaceutically acceptable acid addition salt thereof according to claim 1 wherein said novel 1,4-thiazine derivative is 5-methyl-6-(4-quinolinyl)-2H-1,4-thiazin-3(4H)-one.

14. A 1,4-thiazine derivative represented by the formula I and pharmaceutically acceptable acid addition salt thereof according to claim 1 wherein said novel 1,4-thiazine derivative is 5-methyl-6-(4-pyridazinyl)-2H-1,4-thiazin-3(4H)-one.

15. A 1,4-thiazine derivative represented by the formula I and pharmaceutically acceptable acid addition salt thereof according to claim 1 wherein said novel 1,4-thiazine derivative is 2,5-dimethyl-6-(4-pyridinyl)-2H-1,4-thiazin-3(4H)-one.

16. A 1,4-thiazine derivative represented by the formula I and pharmaceutically acceptable acid addition salt thereof according to claim 1 wherein said novel 1,4-thiazine derivative is 2-ethyl-5-methyl-6-(4-pyridinyl)-2H-1,4-thiazin-3(4H)-one.

17. A 1,4-thiazine derivative represented by the formula I and pharmaceutically acceptable acid additon salt thereof according to claim 1 wherein said novel 1,4-thiazine derivative is 5-methyl-6-(3-chloro-4-pyridinyl)-2H-1,4-thiazin-3(4H)-one.

18. A 1,4-thiazine derivative represented by the formula I and pharmaceutically acceptable acid addition salt thereof according to claim 1 wherein said novel 1,4-thiazine derivative is 5-methyl-6-(3-formyl-4-pyridinyl)-2H-1,4-thiazin-3(4H)-one.

19. A 1,4-thiazine derivative represented by the formula I and pharmaceutically acceptable acid addition salt thereof according to claim 1 wherein said novel 1,4-thiazine derivative is 5-methyl-6-(3-cyano-4-pyridinyl)-2H-1,4-thiazin-3(4H)-one.

20. A 1,4-thiazine derivative represented by the formula I and pharmaceutically acceptable acid addition salt thereof according to claim 1 wherein said novel 1,4-thiazine derivative is 5-methyl-2-methylamino-6-(4-pyridinyl)-2H-1,4-thiazin-3(4H)-one.

21. A 1,4-thiazine derivative represented by the formula I and pharmaceutically acceptable acid addition salt thereof according to claim 1 wherein said novel 1,4-thiazine derivative is 2-hydroxyphenyl-5-methyl-6-(4-pyridinyl)-2H-1,4-thiazin-3(4H)-one.

22. A 1,4-thiazine derivative represented by the formula I and pharmaceutically acceptable acid addition salt thereof according to claim 1 wherein said novel 1,4-thiazine derivative is 5-methyl-2-morpholino-6-(4-pyridinyl)-2H-1,4-thiazin-3(4H)-one.

23. A cardiotonic agent comprising a pharmaceutically acceptable excipient and an effective amount of a 1,4-thiazine derivative representated by the formula I or pharmaceutically acceptable acid addition salt thereof:

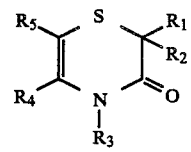

wherein
$R_1$ and $R_2$ represent respectively hydrogen atom, lower alkyl group, lower alkoxy group, unsubstituted amino group, lower alkyl-amino group, aryl-amino group, wherein the aryl-amino is one of phenyl-amino, tolyl-amino, xylyl-amino, mesityl-amino, cumenyl-amino or biphenyl-amino which may be unsubstituted or may be substituted with lower alkyl, lower alkoxy, halogeno, aldehyde, acyl, cyano, nitro or hydroxy, hydroxy group, aryl group wherein the aryl is one of phenyl, tolyl, xylyl, mesityl, cumenyl or bipheynyl which may be unsubstituted or may be substituted with lower alkyl, lower alkoxy, halogeno, aldehyde, acyl, cyano, nitro or hydroxy, or 5- or 6-membered heterocyclic residue; wherein the residue is furyl, thienyl, pyrrolyl, pyrano, pyridinyl, pyridazino, pyrimidino, piperidino, piperazino or morpholino;

$R_3$ and $R_4$ represent hydrogen atom or lower alkyl group; and $R_5$ represents N-containing heterocyclic residue wherein said residue is one of pyridinyl, pyridazinyl, pyrimidinyl, pyrazinyl, quinolinyl, iso-quinolinyl, cinnolinyl, quinazolinyl, quinoxalinyl, phthalazainyl, acridinyl, thiazolyl, piperidinyl, piperazinyl or morpholinyl which may be unsubstituted or may be substituted with lower alkyl, lower alkoxy, halogeno, aldehyde, acyl, cyano, nitro, hydroxy or lower alkoxycarbonyl, and is not pyridinyl group when $R_1$ and $R_2$ represent hydrogen atom and $R_3$ and $R_4$ represent hydrogen atom or lower alkyl group.

24. A cardiotonic agent according to claim 23 wherein the 1,4-thiazine derivative is 5-methyl-6-(4-quinolinyl)-2H-1,4-thiazin-3(4H)-one.

25. A cardiotonic agent according to claim 23 wherein the 1,4-thiazine derivative is 5-methyl-6-(4-pyridazinyl)-2H-1,4-thiazin-3(4H)-one.

26. A cardiotonic agent according to claim 23 wherein the 1,4-thiazine derivative is 2,5-dimethyl-6-(4-pyridinyl)-2H-1,4-thiazin-3(4H)-one.

27. A cardiotonic agent according to claim 23 wherein the 1,4-thiazine derivative is 2-ethyl-5-methyl-6-(4-pyridinyl)-2H-1,4-thiazin-3(4H)-one.

28. A cardiotonic agent according to claim 23 wherein the 1,4-thiazine derivative is 5-methyl-6-(3-chloro-4-pyridinyl)-2H-1,4-thiazin-3(4H)-one.

29. A cardiotonic agent according to claim 23 wherein the 1,4-thiazine derivative is 5-methyl-6-(3-formyl-4-pyridinyl)-2H-1,4-thiazin-3(4H)-one.

30. A cardiotonic agent according to claim 23 wherein the 1,4-thiazine derivative is 5-methyl-6-(3-cyano-4-pyridinyl)-2H-1,4-thiazin-3(4H)-one.

31. A cardiotonic agent according to claim 23 wherein the 1,4-thiazine derivative is 5-methyl-2-methylamino-6-(4-pyridinyl)-2H-1,4-thiazin-3(4H)-one.

32. A cardiotonic agent according to claim 23 wherein the 1,4-thiazine derivative is 2-hydroxyphenyl-5-methyl-6-(4-pyridinyl)-2H-1,4-thiazin-3(4H)-one.

33. A cardiotonic agent according to claim 23 wherein the 1,4-thiazine derivative is 5-methyl-2-morpholino-6-(4-pyridinyl)-2H-1,4-thiazin-3(4H)-one.

* * * * *